(12) United States Patent
Blunsden

(10) Patent No.: US 11,911,568 B2
(45) Date of Patent: Feb. 27, 2024

(54) METHODS AND APPARATUS FOR TREATING A RESPIRATORY DISORDER

(71) Applicant: ResMed Pty Ltd, Bella Vista (AU)

(72) Inventor: Christopher Kingsley Blunsden, Newport (AU)

(73) Assignee: ResMed Pty Ltd (AU)

( * ) Notice: Subject to any disclaimer, the term of this patent is extended or adjusted under 35 U.S.C. 154(b) by 925 days.

(21) Appl. No.: 15/733,254

(22) PCT Filed: Dec. 21, 2018

(86) PCT No.: PCT/AU2018/051377
§ 371 (c)(1),
(2) Date: Jun. 17, 2020

(87) PCT Pub. No.: WO2019/119054
PCT Pub. Date: Jun. 27, 2019

(65) Prior Publication Data
US 2020/0384238 A1 Dec. 10, 2020

(30) Foreign Application Priority Data

Dec. 21, 2017 (AU) .............................. 2017905137
Sep. 26, 2018 (AU) .............................. 2018903634

(51) Int. Cl.
A61M 16/00 (2006.01)
A61M 16/20 (2006.01)
(Continued)

(52) U.S. Cl.
CPC ...... *A61M 16/208* (2013.01); *A61M 16/0677* (2014.02); *A61M 16/101* (2014.02);
(Continued)

(58) Field of Classification Search
CPC ............ A61M 16/208; A61M 16/0677; A61M 16/101; A61M 16/204; A61M 16/1055;
(Continued)

(56) References Cited

U.S. PATENT DOCUMENTS 5,101,656 A 4/1992 Miller
8,875,707 B2 11/2014 Aylsworth
(Continued)

FOREIGN PATENT DOCUMENTS

CA 2793228 C 2/2015
WO 2004068080 A2 8/2004
(Continued)

OTHER PUBLICATIONS

The Extended European Search Report for European Patent Application No. 18890745.5, dated Aug. 9, 2021.
(Continued)

*Primary Examiner* — Steven O Douglas
(74) *Attorney, Agent, or Firm* — Botos Churchill IP Law LLP

(57) ABSTRACT

Apparatus provide gas sensing operations such as for oxygen concentration sensing with an oxygen concentrator. In some versions, gas concentration sensing apparatus with pressure, temperature and/or mass flow sensors measure characteristics of a gas mixture in a vessel. A controller of the apparatus may estimate concentration of a constituent gas in the gas mixture as a function of the measured pressure, temperature and mass flow rate. In some versions, the sensing apparatus may measure a thermal conductivity of enriched gas, and, with a controller, estimate concentration of argon in the enriched gas from the thermal conductivity. The controller may estimate concentration of oxygen in the enriched gas from the concentration of argon. In some versions, an oxygen concentrator may have a mass flow
(Continued)

sensor and a controller configured to trigger bolus delivery and/or measure oxygen concentration, and/or regulate bolus profile based on signals from the mass flow sensor.

20 Claims, 12 Drawing Sheets

(51) Int. Cl.
    *A61M 16/06*     (2006.01)
    *A61M 16/10*     (2006.01)

(52) U.S. Cl.
    CPC ....... *A61M 16/204* (2014.02); *A61M 16/1055* (2013.01); *A61M 2016/0027* (2013.01); *A61M 2016/1025* (2013.01); *A61M 2202/0208* (2013.01); *A61M 2205/3327* (2013.01); *A61M 2205/3334* (2013.01); *A61M 2205/3368* (2013.01); *A61M 2230/42* (2013.01)

(58) Field of Classification Search
    CPC .. A61M 2016/0027; A61M 2016/1025; A61M 2202/0208; A61M 2205/3327; A61M 2205/3334; A61M 2205/3368; A61M 2230/42
    See application file for complete search history.

(56) References Cited

U.S. PATENT DOCUMENTS

| | | |
|---|---|---|
| 2004/0060445 A1 | 4/2004 | Fujimoto |
| 2008/0053310 A1 | 3/2008 | Bliss et al. |
| 2009/0065007 A1 | 3/2009 | Wilkinson |
| 2015/0059742 A1 | 3/2015 | Wilkinson et al. |
| 2018/0143051 A1 | 5/2018 | Bentley et al. |

FOREIGN PATENT DOCUMENTS

| | | |
|---|---|---|
| WO | 2012033839 A2 | 3/2012 |
| WO | 2017106636 A1 | 6/2017 |

OTHER PUBLICATIONS

Demin, et al., "Sensor for Measuring the Oxygen Concentration in Gas Mixtures with Unsteady Pressure", Solid State Ionics, vol. 112, 1998, pp. 355-359.

Toda, et al., "High-speed Gas Concentration Measurement Using Ultrasound", Sensors and Actuators A, vol. 144, 2008, pp. 1-6.

Williams, et al., "01AP10-1 Real-time Measurement of Xenon in a Binary Gas Mixture Using Ultrasound Time-of-flight: a Feasibility Study", Euroanaesthesia, 2017, vol. 34, pp. 34-35.

PCT Written Opinion of the International Searching Authority dated Apr. 15, 2019.

Morini, Gian Luca, et al., ""A critical review of the measurement techniques for the analysis of gas microflows through microchannels."", Experimental Thermal and Fluid Science, vol. 35, No. 6, (2011), pp. 849-865.

Van Der Wouden, Egbert, et al., ""Multi parameter flow meter for on-line measurement of gas mixture composition."", Micromachines, vol. 6, No. 4, (2015), pp. 452-461.

Zhu, Y. Q., et al., ""Modelling and simulation of a thermal flow sensor for determining the flow speed and thermal properties of binary gas mixtures."", Procedia Engineering, vol. 168,, (2016), pp. 1028-1031.

METHODS AND APPARATUS FOR TREATING A RESPIRATORY DISORDER

CROSS-REFERENCE TO RELATED APPLICATIONS

The present application is a national phase entry under 35 U.S.C. § 371 of International Application No. PCT/AU2018/051377 filed Dec. 21, 2018, published in English, which claims priority from Australian Provisional Patent Application No. 2018903634 filed Sep. 26, 2018 and Australian Provisional Patent Application No. 2017905137 filed Dec. 21, 2017, all of which are incorporated herein by reference.

FIELD OF THE TECHNOLOGY

The present technology relates generally to methods and apparatus for treating respiratory disorders, and more specifically to methods and apparatus for measuring gas concentration such as that of the oxygen concentration of oxygen enriched gas produced by an oxygen concentrator.

DESCRIPTION OF THE RELATED ART

There are many users that require supplemental oxygen as part of Long Term Oxygen Therapy (LTOT). Currently, the vast majority of users that are receiving LTOT are diagnosed under the general category of Chronic Obstructive Pulmonary Disease (COPD). This general diagnosis includes such common diseases as Chronic Asthma, Emphysema, and several other cardio-pulmonary conditions. Other users may also require supplemental oxygen, for example, obese individuals to maintain elevated activity levels, or infants with cystic fibrosis or broncho-pulmonary dysplasia.

Doctors may prescribe oxygen concentrators or portable tanks of medical oxygen for these users. Usually a specific continuous oxygen flow rate is prescribed (e.g., 1 litre per minute (LPM), 2 LPM, 3 LPM, etc.). Experts in this field have also recognized that exercise for these users provide long term benefits that slow the progression of the disease, improve quality of life and extend user longevity. Most stationary forms of exercise like treadmills and stationary bicycles, however, are too strenuous for these users. As a result, the need for mobility has long been recognized. Until recently, this mobility has been facilitated by the use of small compressed oxygen tanks. The disadvantage of these tanks is that they have a finite amount of oxygen and they are heavy, weighing about 50 pounds, when mounted on a cart with dolly wheels.

Oxygen concentrators have been in use for about 50 years to supply users suffering from respiratory insufficiency with supplemental oxygen. Traditional oxygen concentrators used to provide these flow rates have been bulky and heavy making ordinary ambulatory activities with them difficult and impractical. Recently, companies that manufacture large stationary home oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed.

It is advantageous to know the concentration of oxygen in the oxygen enriched gas delivered by a POC. Moreover, in some jurisdictions it is actually a regulatory requirement to sound an alarm if the concentration falls below some threshold. An oxygen sensor is a device capable of detecting the presence of and/or measuring the concentration of oxygen in a gas. Species of oxygen sensors include, but are not limited to, ultrasonic oxygen sensors, electrical oxygen sensors, and optical oxygen sensors. However, each of these species has one or more disadvantages. In particular, ultrasonic oxygen sensors are typically expensive and large due to the length of path needed to accurately measure a path delay and hence the speed of sound. A need therefore exists for a new species of oxygen sensor that ameliorates the disadvantages of existing species.

SUMMARY OF THE TECHNOLOGY

Some versions of the present technology may include methods and apparatus that measure a concentration of a constituent gas in a gas mixture, such as oxygen in the oxygen enriched gas delivered by a POC.

In some versions, the apparatus may comprise a pressure sensor and a temperature sensor in a chamber containing the gas mixture, and a mass flow sensor adjacent to the chamber. A processing method uses the pressure and temperature of the gas in the chamber, as measured by the pressure and temperature sensors respectively, at the start and end of an interval over which a mass flow sensor measures a change in mass of the gas mixture in the vessel, along with the change in mass, to estimate the specific gas constant of the gas mixture in the chamber from the ideal or universal gas law. The concentration of the gas may be estimated from the specific gas constant of the gas mixture.

Optionally, in some versions, the apparatus may comprise an argon concentration sensor configured to sense the argon concentration in the oxygen enriched gas using the thermal properties of the oxygen enriched gas. Thermal properties are particularly suitable for sensing argon concentration in a mixture of nitrogen, oxygen, and argon because argon's thermal properties are significantly different from those of oxygen and nitrogen. The argon concentration may be used to infer the oxygen concentration in the oxygen enriched gas.

Some versions of the present technology may include a method of estimating a concentration of a constituent gas in a gas mixture. The method may include measuring pressure of the gas mixture. The method may include measuring temperature of the gas mixture. The method may include measuring mass flow rate of the gas mixture. The method may include determining an estimate of the concentration of the constituent gas in the gas mixture as a function of the measured pressure, temperature, and mass flow rate.

In some versions, the method may include measuring a first pressure and a first temperature of the gas mixture in a vessel at a start of an interval. The method may include measuring a second pressure and a second temperature of the gas mixture in the vessel at an end of the interval. The method may include measuring a change in mass of the gas mixture in the vessel over the interval. The method may include estimating a specific gas constant of the gas mixture from the first pressure, the first temperature, the second pressure, the second temperature, and the change in mass. The method may include estimating the concentration of the constituent gas in the gas mixture from the estimate of the specific gas constant.

In some versions, measuring the change in mass of the gas mixture in the vessel may include integrating a signal representing a mass flow rate of the gas mixture entering or leaving the vessel over an interval between measuring the first pressure and the first temperature, and measuring the second pressure and the second temperature. The signal may represent a mass flow rate of the gas mixture leaving the vessel. The signal may represent a mass flow rate of the gas mixture entering the vessel. The signal may represent a difference between a mass flow rate of the gas mixture leaving the vessel and a mass flow rate of the gas mixture entering the vessel. Estimating the specific gas constant may include multiplication by a calibration constant. The method may include estimating the concentration of the constituent gas using the specific gas constants of the gases in the gas mixture. Estimating the concentration of the constituent gas may use a measure of volume of the vessel. The gas mixture may be an enriched mixture of three or more gases. Estimating the concentration of the constituent gas may be based on starting concentrations of the gases in the enriched mixture. The gas may be a non-removed gas in the enriched mixture.

In some versions, the method may include controlling an operation of an oxygen concentrator based on the determined estimate of the concentration of the constituent gas in the gas mixture. The operation of the oxygen concentrator may include a pressure swing adsorption process. The operation of the oxygen concentrator may include triggering an alarm.

Some versions of the present technology may include a gas concentration sensing apparatus. The apparatus may include a pressure sensor configured to measure pressure of a gas mixture in a vessel. The apparatus may include a temperature sensor configured to measure temperature of the gas mixture in the vessel. The apparatus may include a mass flow sensor configured to generate a mass flow rate signal representing mass flow rate of the gas mixture entering or leaving the vessel. The apparatus may include a controller coupled to the pressure sensor, the temperature sensor and the mass flow sensor. The controller may be configured to determine an estimate of the concentration of a constituent gas in the gas mixture as a function of the measured pressure, temperature, and mass flow rate.

In some versions, the controller may be configured to calculate a change in mass of the gas mixture in the vessel over an interval using the mass flow rate signal. The controller may be configured to estimate a specific gas constant of the gas mixture from a first pressure measurement and a first temperature measurement at a start of the interval, a second pressure measurement and a second temperature measurement at an end of the interval, and the change in mass. The controller may be configured to estimate the concentration of the constituent gas in the gas mixture from the estimate of the specific gas constant of the gas mixture. The mass flow sensor may be positioned at an inlet of the vessel. The mass flow sensor may be positioned at an outlet of the vessel. The apparatus may include a second mass flow sensor positioned at an outlet of the vessel. The second mass flow sensor may be configured to generate a second mass flow rate signal representing a mass flow rate of the gas mixture leaving the vessel. The controller may be configured to calculate the change in mass of the gas mixture in the vessel over the interval using the second mass flow rate signal.

In some versions, the apparatus may include an oxygen concentrator. The controller may be configured to control an operation of the oxygen concentrator based on the determined estimate of the concentration of the constituent gas in the gas mixture. The operation of the oxygen concentrator based on the determined estimate of the concentration of the constituent gas in the gas mixture may include a pressure swing adsorption process. The operation of the oxygen concentrator based on the determined estimate of the concentration of the constituent gas in the gas mixture may include triggering an alarm.

Some versions of the present technology may include a method of estimating a concentration of a constituent gas in a gas mixture. The method may include estimating a specific gas constant of the gas mixture from measurements of properties of the gas mixture in a vessel. The properties may include pressure at a start of an interval and at an end of the interval. The properties may include temperature at the start of the interval and at the end of the interval. The properties may include a change of mass over the interval. The method may include estimating the concentration of the constituent gas in the gas mixture from the specific gas constant estimate. The method may include estimating the specific gas constant of the gas mixture uses a measure of volume of the vessel. Estimating the concentration of the constituent gas may be based on specific gas constants of gases in the gas mixture. The gas mixture may be an enriched mixture. Estimating the concentration of the constituent gas may be based on starting concentrations of the gases in the enriched mixture. The gas may be a non-removed gas in the enriched mixture.

In some versions, the method may include controlling an operation of an oxygen concentrator based on the estimated concentration of the constituent gas in the gas mixture. The operation may include one or both of (1) a pressure swing adsorption process, and (2) triggering an alarm.

Some versions of the present technology may include a gas concentration sensing apparatus. The apparatus may include a pressure sensor configured to measure a pressure of a gas mixture in a vessel. The apparatus may include a temperature sensor configured to measure a temperature of the gas mixture in the vessel. The apparatus may include a mass flow sensor configured to measure a mass flow rate of the gas mixture entering or leaving the vessel. The apparatus may include a controller. The controller may be configured to estimate a specific gas constant of the gas mixture from measurements of properties of the gas mixture in a vessel. The properties may include any one or more of pressure at a start of an interval and at an end of the interval, measured using the pressure sensor; temperature at the start of the interval and at the end of the interval, measured using the temperature sensor; and/or a change of mass over the interval, measured using the mass flow sensor. The controller may be configured to estimate the concentration of a constituent gas in the gas mixture from the specific gas constant estimate.

In some versions, the mass flow sensor may be positioned at an inlet of the vessel. The mass flow sensor may be positioned at an outlet of the vessel. The apparatus may further include a second mass flow sensor positioned at an outlet of the vessel. The second mass flow sensor may be configured to measure a mass flow rate of the gas mixture leaving the vessel. The controller may be configured to measure the change in mass over the interval using the second mass flow sensor. The apparatus may further include an oxygen concentrator. The controller may be configured to control an operation of the oxygen concentrator based on the estimate of the concentration of the constituent gas in the gas mixture. The operation of the oxygen concentrator may include one or both of (1) a pressure swing adsorption process, and (2) triggering an alarm.

Some versions of the present technology may include apparatus. The apparatus may include means for generating a measure of pressure of a gas mixture in a vessel. The apparatus may include means for generating a measure of temperature of the gas mixture in the vessel. The apparatus may include means for generating a mass flow rate signal representing a mass flow rate of the gas mixture entering or leaving the vessel. The apparatus may include means for estimating a concentration of a constituent gas in the gas mixture as a function of the measured pressure, temperature, and mass flow rate.

Some versions of the present technology may include a method of estimating concentration of oxygen in oxygen enriched gas. The method may include measuring thermal conductivity of the oxygen enriched gas. The method may include estimating concentration of argon in the oxygen enriched gas from the thermal conductivity. The method may include estimating concentration of oxygen in the oxygen enriched gas from the concentration of argon.

In some versions, the measuring thermal conductivity of the oxygen enriched gas may include estimating a temperature of a flow of the oxygen enriched gas. The measuring thermal conductivity of the oxygen enriched gas may include measuring a temperature of a self-heated element in thermal communication with the flow of oxygen enriched gas. The measuring thermal conductivity of the oxygen enriched gas may include estimating the thermal conductivity from a difference between the temperature of the flow and the temperature of the self-heated element. The method may further include measuring flow rate of the flow of oxygen enriched gas. Estimating the thermal conductivity may estimates the thermal conductivity from the difference and the measured flow rate. Estimating the concentration of argon may include interpolating between values in a lookup table that tabulates thermal conductivity against argon concentration. The method may further include controlling an operation of an oxygen concentrator based on the estimated concentration of oxygen. The operation may include one or both of (1) a pressure swing adsorption process, and (2) triggering an alarm.

Some versions of the present technology may include an oxygen concentration sensing apparatus. The apparatus may include a sensor configured to measure a thermal conductivity of oxygen enriched gas. The apparatus may include a controller. The controller may be configured to estimate concentration of argon in the oxygen enriched gas from the thermal conductivity. The controller may be configured to estimate concentration of oxygen in the oxygen enriched gas from the concentration of argon. The sensor may include a temperature sensor configured to sense the temperature of a flow of the oxygen enriched gas. The sensor may include a self-heated element in thermal communication with the flow of oxygen enriched gas.

In some versions, the controller may be further configured to estimate the thermal conductivity from a difference between the temperature of the flow and the temperature of the self-heated element. The apparatus may further include a flow rate sensor configured to generate a signal representative of the flow rate of the oxygen enriched gas. The controller may be configured to estimate the thermal conductivity from the difference and the flow rate of the oxygen enriched gas. The apparatus may further include an oxygen concentrator. The controller may be configured to control an operation of the oxygen concentrator based on the estimate of the concentration of oxygen. The operation of the oxygen concentrator may include one or both of (1) a pressure swing adsorption process, and (2) triggering an alarm.

Some versions of the present technology may include apparatus. The apparatus may include means for measuring thermal conductivity of oxygen enriched gas. The apparatus may include means for estimating concentration of argon in the oxygen enriched gas from the thermal conductivity. The apparatus may include means for estimating concentration of oxygen in the oxygen enriched gas from the concentration of argon.

Some versions of the present technology may include an oxygen concentrator apparatus. The oxygen concentrator apparatus may include an outlet, the outlet suitable for pneumatic coupling with a delivery device, the delivery device for delivering, in use, oxygen enriched gas to a patient. The oxygen concentrator apparatus may include at least two canisters including gas separation adsorbent. The gas separation adsorbent may be configured for gas separation of at least some nitrogen from air in the at least two canisters to produce the oxygen enriched gas. The oxygen concentrator apparatus may include a compression system that may include a compressor coupled to at least one of the canisters to compress air during operation to promote the gas separation. The oxygen concentrator apparatus may include an accumulator coupled to one or more of the canisters, to accumulate the oxygen enriched gas produced in one or more of the canisters during use. The accumulator may be pneumatically coupled to the outlet. The oxygen concentrator apparatus may include a flow rate sensor pneumatically coupled to the accumulator and the outlet. The flow rate sensor may be configured to generate at least a flow rate signal. The oxygen concentrator apparatus may include a controller, including one or more processors, and a set of valves coupled to the controller. The controller may be configured to control operation of the set of valves to (a) produce the oxygen enriched gas into the accumulator and (b) release the produced oxygen enriched gas from the accumulator in at least one bolus. The controller may be configured to receive the flow rate signal from the flow rate sensor. The controller may be configured to evaluate the flow rate signal to detect an onset of inhalation by the patient when in use. The controller may be configured to control a delivery valve of the set of valves to trigger release, to the outlet, of the at least one bolus based on the detected onset from the evaluation of the flow rate signal from the flow rate sensor. The controller may be configured to monitor the flow rate signal during release of the at least one bolus.

In some versions, the flow rate sensor may be a thermal mass flow sensor. The controller may be further configured to receive a thermal conductivity signal from the thermal mass flow sensor. The controller may be further configured to estimate concentration of oxygen of the oxygen enriched gas based on the received thermal conductivity signal from the thermal mass flow sensor. The controller may be further configured to evaluate the estimated concentration of oxygen. The controller may be further configured to generate an alarm signal based on the evaluation of the estimated concentration of oxygen. The controller may be further configured to control the delivery valve to adjust an amplitude profile of the at least one bolus based on the monitored flow rate signal from the flow rate sensor. The delivery valve may include a multi-port valve including a first port pneumatically coupled to a tap, a second port pneumatically coupled to the outlet, and/or a third port pneumatically coupled to the accumulator. In some versions, to sense the onset of inhalation, the controller may be configured to set the delivery valve to pneumatically couple (1) the first port to the tap with (2) the second port to the outlet. To deliver the at least one bolus, the controller may be configured to set the delivery valve to pneumatically couple (1) the second port to the outlet with (2) the third port to the accumulator. The oxygen concentrator apparatus may include a tap to atmosphere in a pneumatic path between the outlet and the accumulator. The flow rate sensor may be positioned proximate to the tap to measure flow rate through the tap from atmosphere to the pneumatic path. The tap may include a high impedance tubing configured to limit amount of flow through the tap during bolus release. The oxygen concentrator apparatus may include a passive valve in parallel with the tap to atmosphere. The passive valve may be configured to permit different flow rates through the passive valve depending on direction of flow through the passive valve.

Some versions of the present technology may include an oxygen concentrator apparatus. The oxygen concentrator apparatus may include an outlet. The outlet may be suitable for pneumatic coupling with a delivery device. The delivery device may be for delivering, in use, oxygen enriched gas to a patient. The oxygen concentrator apparatus may include at least one or two canisters including gas separation adsorbent. The gas separation adsorbent may be configured for gas separation of at least some nitrogen from air in the canister(s) to produce the oxygen enriched gas. The oxygen concentrator apparatus may include a compression system that may include a compressor coupled to at least one of the canisters to compress air during operation to promote the gas separation. The oxygen concentrator apparatus may include an accumulator coupled to one or more of the canisters, to accumulate the oxygen enriched gas produced in one or more of the canisters during use. The accumulator may be pneumatically coupled to the outlet. The oxygen concentrator apparatus may include a thermal mass flow sensor that may be pneumatically coupled to the accumulator and/or the outlet. The thermal mass flow sensor may be configured to generate at least a flow rate signal and/or a thermal conductivity signal. The oxygen concentrator apparatus may include a controller, including one or more processors, and a set of valves coupled to the controller. The controller may be configured to control operation of the set of valves to (a) produce the oxygen enriched gas into the accumulator and/or (b) release the produced oxygen enriched gas from the accumulator in at least one bolus. The controller may be further configured to receive the flow rate signal from the thermal mass flow sensor. The controller may be further configured to receive the thermal conductivity signal from the thermal mass flow sensor. The controller may be further configured to control a delivery valve of the set of valves to trigger release, to the outlet, of the at least one bolus. The controller may be further configured to monitor the flow rate signal during release of the at least one bolus. The controller may be further configured to estimate concentration of oxygen in the at least one bolus based on the received thermal conductivity signal from the thermal mass flow sensor.

In some versions, the controller may be further configured to evaluate the estimated concentration of oxygen. The controller may be further configured to generate an alarm signal based on the evaluation of the estimated concentration of oxygen. The controller may be further configured to control the delivery valve to adjust an amplitude profile of the at least one bolus based on the monitored flow rate signal from the thermal mass flow sensor.

Some versions of the present technology may include an oxygen concentrator apparatus. The oxygen concentrator apparatus may include an outlet suitable for pneumatic coupling with a delivery device. The delivery device may be for delivering, in use, oxygen enriched gas to a patient. The oxygen concentrator apparatus may include at least one or two canisters including gas separation adsorbent. The gas separation adsorbent may be configured for gas separation of at least some nitrogen from air in the canister(s) to produce the oxygen enriched gas. The oxygen concentrator apparatus may include a compression system that may include a compressor coupled to at least one of the canisters to compress air during operation to promote the gas separation. The oxygen concentrator apparatus may include an accumulator coupled to one or more of the canisters, to accumulate the oxygen enriched gas produced in one or more of the canisters during use. The accumulator may be pneumatically coupled to the outlet. The oxygen concentrator apparatus may include a thermal mass flow sensor pneumatically coupled to the accumulator and/or the outlet. The thermal mass flow sensor may be configured to generate at least a flow rate signal and/or a thermal conductivity signal. The oxygen concentrator apparatus may include a controller, including one or more processors, and a set of valves coupled to the controller. The controller may be configured to control operation of the set of valves to (a) produce the oxygen enriched gas into the accumulator and/or (b) release the produced oxygen enriched gas from the accumulator in at least one bolus. The controller may be further configured to receive the flow rate signal from the thermal mass flow sensor. The controller may be further configured to receive the thermal conductivity signal from the thermal mass flow sensor. The controller may be further configured to evaluate the flow rate signal to detect an onset of inhalation by the patient when in use. The controller may be further configured to control a delivery valve of the set of valves to trigger release, to the outlet, of the at least one bolus based on the detected onset from the evaluation of the flow rate signal from the thermal mass flow sensor. The controller may be further configured to estimate concentration of oxygen in the bolus based on the received thermal conductivity signal from the thermal mass flow sensor.

In some versions, the controller may be further configured to evaluate the estimated concentration of oxygen. The controller may be further configured to generate an alarm signal based on the evaluation of the estimated concentration of oxygen. The oxygen concentrator apparatus may include a tap to atmosphere in a pneumatic path between the outlet and/or the accumulator. The thermal mass flow sensor may be positioned proximate to the tap to measure flow rate through the tap from atmosphere to the pneumatic path. The oxygen concentrator apparatus may include a passive valve in the tap to atmosphere. The passive valve may be configured to permit different flow rates through the passive valve depending on direction of flow through the passive valve. The passive valve may be configured with a small dead band at low positive pressures. The oxygen concentrator apparatus may include a high impedance tubing in parallel with the tap to atmosphere. The high impedance tubing may be configured to limit amount of flow through the tubing during release of the at least one bolus. The controller may be further configured to monitor the flow rate signal during release of the at least one bolus. The controller may be further configured to control the delivery valve to adjust an amplitude profile of the at least one bolus based on the monitored flow rate signal from the thermal mass flow sensor.

Some versions of the present technology may include a method of a controller of an oxygen concentrator apparatus. The method may include receiving a flow rate signal in the controller. The flow rate signal may be generated with a flow rate sensor that may be pneumatically coupled to (1) an accumulator for oxygen enriched gas produced by the oxygen concentrator apparatus, and/or (2) an outlet for the oxygen enriched gas. The method may include evaluating, in the controller, the flow rate signal to detect an onset of inhalation by a user of the oxygen concentrator apparatus. The method may include controlling, by the controller, a delivery valve to trigger release, to the outlet, of at least one bolus based on the detected onset from the evaluation of the flow rate signal from the flow rate sensor. The method may include monitoring, in the controller, the flow rate signal during release of the at least one bolus.

In some versions, the flow rate sensor may be a thermal mass flow sensor. The method may include receiving, in the controller, a thermal conductivity signal from the thermal mass flow sensor. The method may include estimating in the controller, concentration of oxygen of the oxygen enriched gas based on the received thermal conductivity signal from the thermal mass flow sensor. The method may include evaluating, in the controller, the estimated concentration of oxygen. The method may include generating, with the controller, an alarm signal based on the evaluation of the estimated concentration of oxygen. The method may include controlling, with the controller, the delivery valve to adjust an amplitude profile of the at least one bolus based on the monitored flow rate signal from the flow rate sensor. The delivery valve may include a multi-port valve including a first port pneumatically coupled to a tap, a second port pneumatically coupled to the outlet, and a third port pneumatically coupled to the accumulator. The controller may controls setting of the delivery valve to pneumatically couple (1) the first port to the tap with (2) the second port to the outlet. To deliver the at least one bolus, the controller may control setting of the delivery valve to pneumatically couple (1) the second port to the outlet with (2) the third port to the accumulator. The flow rate sensor may be positioned proximate to a tap to measure flow rate through the tap from atmosphere to a pneumatic path. The tap may be pneumatically coupled to atmosphere and the pneumatic path may be between the outlet and the accumulator. The tap may include a high impedance tubing configured to limit amount of flow through the tap during bolus release. A passive valve may be in parallel with the tap to atmosphere. The passive valve may be configured to permit different flow rates through the passive valve depending on direction of flow through the passive valve.

Some versions of the present technology may include a method of a controller of an oxygen concentrator apparatus. The method may include receiving, in the controller, a flow rate signal and a thermal conductivity signal. The flow rate signal and the thermal conductivity signal may be generated with a thermal mass flow sensor pneumatically coupled to (1) an accumulator for oxygen enriched gas produced by the oxygen concentrator apparatus, and/or (2) an outlet for the oxygen enriched gas. The method may include controlling, by the controller, a delivery valve to trigger release, to the outlet, of at least one bolus. The method may include monitoring, in the controller, the flow rate signal during release of the at least one bolus. The method may include estimating, in the controller, concentration of oxygen in the at least one bolus based on the received thermal conductivity signal from the thermal mass flow sensor.

In some versions, the method may include evaluating, in the controller, the estimated concentration of oxygen. The method may include generating, with the controller, an alarm signal based on the evaluation of the estimated concentration of oxygen. The method may further include controlling, by the controller, the delivery valve to adjust an amplitude profile of the at least one bolus based on the monitored flow rate signal from the thermal mass flow sensor.

Some versions of the present technology may include a method of a controller of an oxygen concentrator apparatus. The method may include receiving, in the controller, a flow rate signal and a thermal conductivity signal. The flow rate signal and the thermal conductivity signal may be generated with a thermal mass flow sensor. The thermal mass flow sensor may be pneumatically coupled to (1) an accumulator for oxygen enriched gas produced by the oxygen concentrator apparatus, and/or (2) an outlet for the oxygen enriched gas. The method may include evaluating, in the controller, the flow rate signal to detect an onset of inhalation by a user of the oxygen concentrator apparatus. The method may include controlling, by the controller, a delivery valve to trigger release, to the outlet, of at least one bolus based on the detected onset from the evaluation of the flow rate signal from the thermal mass flow sensor. The method may include estimating, in the controller, concentration of oxygen in the bolus based on the received thermal conductivity signal from the thermal mass flow sensor.

In some versions, the method may include evaluating, in the controller, the estimated concentration of oxygen. The method may include generating, with the controller, an alarm signal based on the evaluation of the estimated concentration of oxygen. The thermal mass flow sensor may be positioned proximate to a tap to measure flow rate through the tap from atmosphere to a pneumatic path. The tap may be pneumatically coupled to atmosphere and the pneumatic path may be between the outlet and the accumulator. A passive valve may be in the tap to atmosphere. The passive valve may be configured to permit different flow rates through the passive valve depending on direction of flow through the passive valve. The passive valve may be configured with a small dead band at low positive pressures. A high impedance tubing may be in parallel with the tap to atmosphere. The high impedance tubing may be configured to limit amount of flow through the high impedance tubing during release of the at least one bolus. The method may include monitoring, in the controller, the flow rate signal during release of the at least one bolus. The method may include controlling, with the controller, the delivery valve to adjust an amplitude profile of the at least one bolus based on the monitored flow rate signal from the thermal mass flow sensor.

BRIEF DESCRIPTION OF THE DRAWINGS

Advantages of the present technology will become apparent to those skilled in the art with the benefit of the following detailed description of embodiments and upon reference to the accompanying drawings in which.

Figure 1:
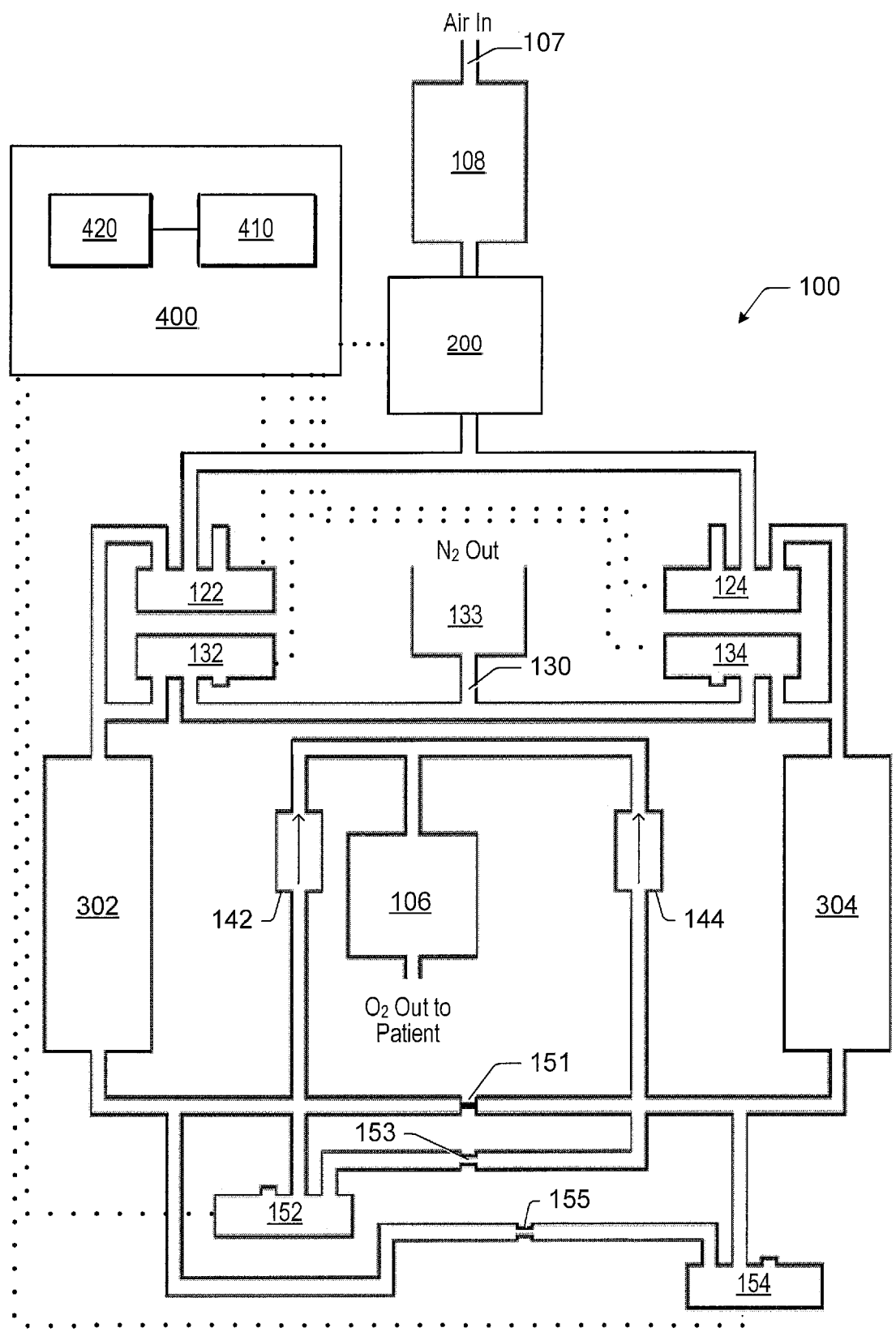
FIG. 1 depicts a schematic diagram of the components of an oxygen concentrator.

While the technology is susceptible to various modifications and alternative forms, specific embodiments thereof are shown by way of example in the drawings and will herein be described in detail. It should be understood, however, that the drawings and detailed description thereto are not intended to limit the technology to the particular form disclosed, but on the contrary, the intention is to cover all modifications, equivalents, and alternatives falling within the spirit and scope of the present technology as defined by the appended claims.

DETAILED DESCRIPTION OF THE EMBODIMENTS

It is to be understood the present technology is not limited to particular devices or methods, which may, of course, vary. It is also to be understood that the terminology used herein is for the purpose of describing particular embodiments only, and is not intended to be limiting. Headings are for organizational purposes only and are not meant to be used to limit or interpret the description or claims. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to."

The term "coupled" as used herein means either a direct connection or an indirect connection (e.g., one or more intervening connections) between one or more objects or components. The phrase "connected" means a direct connection between objects or components such that the objects or components are connected directly to each other. As used herein the phrase "obtaining" a device means that the device is either purchased or constructed.

Oxygen concentrators take advantage of pressure swing adsorption (PSA). Pressure swing adsorption may involve using a compressor to increase gas pressure inside a canister that contains particles of a gas separation adsorbent. As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace gases. If a gas mixture such as air, for example, is passed under pressure through a vessel containing a gas separation adsorbent bed that attracts nitrogen more strongly than it does oxygen, part or all of the nitrogen will stay in the bed, and the gas coming out of the vessel will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched gas. By alternating canisters in a two-canister system, one canister can be collecting oxygen while the other canister is being purged (resulting in a continuous separation of the oxygen from the nitrogen). In this manner, oxygen can be accumulated out of the air for a variety of uses include providing supplemental oxygen to users.

FIG. 1 illustrates a schematic diagram of an oxygen concentrator 100, according to an embodiment. Oxygen concentrator 100 may concentrate oxygen out of an air stream to provide oxygen enriched gas to a user. As used herein, "oxygen enriched gas" is composed of at least about 50% oxygen, at least about 60% oxygen, at least about 70% oxygen, at least about 80% oxygen, at least about 90% oxygen, at least about 95% oxygen, at least about 98% oxygen, or at least about 99% oxygen.

Oxygen concentrator 100 may be a portable oxygen concentrator. For example, oxygen concentrator 100 may have a weight and size that allows the oxygen concentrator to be carried by hand and/or in a carrying case. In one embodiment, oxygen concentrator 100 has a weight of less than about 20 lbs., less than about 15 lbs., less than about 10 lbs, or less than about 5 lbs. In an embodiment, oxygen concentrator 100 has a volume of less than about 1000 cubic inches, less than about 750 cubic inches; less than about 500 cubic inches, less than about 250 cubic inches, or less than about 200 cubic inches.

Nitrogen may be separated from ambient air by pressurising ambient air in canisters 302 and 304, which include a gas separation adsorbent. Gas separation adsorbents useful in an oxygen concentrator are capable of separating at least nitrogen from an air stream to produce oxygen enriched gas. Examples of gas separation adsorbents include molecular sieves that are capable of separation of nitrogen from an air stream. Examples of adsorbents that may be used in an oxygen concentrator include, but are not limited to, zeolites (natural) or synthetic crystalline aluminosilicates that separate nitrogen from oxygen in an air stream under elevated pressure. Examples of synthetic crystalline aluminosilicates that may be used include, but are not limited to: OXYSIV adsorbents available from UOP LLC, Des Plaines, IW; SYLOBEAD adsorbents available from W. R. Grace & Co, Columbia, MD; SILIPORITE adsorbents available from CECA S.A. of Paris, France; ZEOCHEM adsorbents available from Zeochem AG, Uetikon, Switzerland; and AgLi-LSX adsorbent available from Air Products and Chemicals, Inc., Allentown, PA.

As shown in FIG. 1, air may enter the oxygen concentrator through air inlet 107. Air may be drawn into air inlet 107 by compression system 200. Compression system 200 may draw in air from the surroundings of the oxygen concentrator and compress the air, forcing the compressed air into one or both canisters 302 and 304. In an embodiment, an inlet muffler 108 may be coupled to air inlet 107 to reduce sound produced by air being pulled into the oxygen concentrator by compression system 200. In an embodiment, inlet muffler 108 may be a moisture and sound absorbing muffler. For example, a water absorbent material (such as a polymer water absorbent material or a zeolite material) may be used to both absorb water from the incoming air and to reduce the sound of the air passing into the air inlet 107.

Compression system 200 may include one or more compressors capable of compressing air. Pressurized air, produced by compression system 200, may be forced into one or both of the canisters 302 and 304. In some embodiments, the ambient air may be pressurized in the canisters to a pressure of approximately 30 pounds per square inch (psi). Other pressures may also be used, depending on the type of gas separation adsorbent disposed in the canisters.

Coupled to each canister 302/304 are inlet valves 122/124 and outlet valves 132/134. As shown in FIG. 1, inlet valve 122 is coupled to canister 302 and inlet valve 124 is coupled to canister 304. Outlet valve 132 is coupled to canister 302 and outlet valve 134 is coupled to canister 304. Inlet valves 122/124 are used to control the passage of air from compression system 200 to the respective canisters. Outlet valves 132/134 are used to release gas from the respective canisters during a venting process. In some embodiments, inlet valves 122/124 and outlet valves 132/134 may be silicon plunger solenoid valves. Other types of valves, however, may be used. Plunger valves offer advantages over other kinds of valves by being quiet and having low leakage.

In some embodiments, a two-step valve actuation voltage may be used to control inlet valves 122/124 and outlet valves 132/134. For example, a high voltage (e.g., 24 V) may be applied to an inlet valve to open the inlet valve. The voltage may then be reduced (e.g., to 7 V) to keep the inlet valve open. Using less voltage to keep a valve open may use less power (Power=Voltage*Current). This reduction in voltage minimizes heat build up and power consumption to extend run time from the battery. When the power is cut off to the valve, it closes by spring action. In some embodiments, the voltage may be applied as a function of time that is not necessarily a stepped response (e.g., a curved downward voltage between an initial 24 V and a final 7 V).

In an embodiment, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. In an embodiment, a controller 400 is electrically coupled to valves 122, 124, 132, and 134. Controller 400 includes one or more processors 410 operable to execute program instructions stored in memory 420. The program instructions are operable to perform various predefined methods that are used to operate the oxygen concentrator. Controller 400 may include program instructions for operating inlet valves 122 and 124 out of phase with each other, i.e., when one of inlet valves 122 or 124 is opened, the other valve is closed. During pressurization of canister 302, outlet valve 132 is closed and outlet valve 134 is opened. Similar to the inlet valves, outlet valves 132 and 134 are operated out of phase with each other. In some embodiments, the voltages and the duration of the voltages used to open the input and output valves may be controlled by controller 400.

Check valves 142 and 144 are coupled to canisters 302 and 304, respectively. Check valves 142 and 144 are one way valves that are passively operated by the pressure differentials that occur as the canisters are pressurized and vented. Check valves 142 and 144 are coupled to canisters to allow oxygen produced during pressurization of the canister to flow out of the canister, and to inhibit back flow of oxygen or any other gases into the canister. In this manner, check valves 142 and 144 act as one way valves allowing oxygen enriched gas to exit the respective canister while pressurized.

The term "check valve", as used herein, refers to a valve that allows flow of a fluid (gas or liquid) in one direction and inhibits back flow of the fluid. Examples of check valves that are suitable for use include, but are not limited to: a ball check valve; a diaphragm check valve; a butterfly check valve; a swing check valve; a duckbill valve; and a lift check valve. Under pressure, nitrogen molecules in the pressurized ambient air are adsorbed by the gas separation adsorbent in the pressurized canister. As the pressure increases, more nitrogen is adsorbed until the gas in the canister is enriched in oxygen. The non-adsorbed gas molecules (mainly oxygen) flow out of the pressurized canister when the pressure in the canister is higher than the pressure on the output side of the check valve coupled to the canister. In one embodiment, the pressure drop of the check valve in the forward direction is less than 1 psi. The break pressure in the reverse direction is greater than 100 psi. It should be understood, however, that modification of one or more components would alter the operating parameters of these valves. If the forward flow pressure is increased, there is, generally, a reduction in oxygen enriched gas production. If the break pressure for reverse flow is reduced or set too low, there is, generally, a reduction in oxygen enriched gas pressure.

In an exemplary embodiment, canister 302 is pressurized by compressed air produced in compression system 200 and passed into canister 302. During pressurization of canister 302 inlet valve 122 is open, outlet valve 132 is closed, inlet valve 124 is closed and outlet valve 134 is open. Outlet valve 134 is opened when outlet valve 132 is closed to allow substantially simultaneous venting of canister 304 while canister 302 is pressurized. Canister 302 is pressurized until the pressure in canister is sufficient to open check valve 142. Oxygen enriched gas produced in canister 302 exits through check valve and, in one embodiment, is collected in accumulator 106.

After some time the gas separation adsorbent will become saturated with nitrogen and will be unable to separate significant amounts of nitrogen from incoming air. In the embodiment described above, when the gas separation adsorbent in canister 302 reaches this saturation point, the inflow of compressed air is stopped and canister 302 is vented to remove nitrogen. During venting, inlet valve 122 is closed, and outlet valve 132 is opened. While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

During venting of canister 302, outlet valve 132 is opened allowing pressurized gas (mainly nitrogen) to exit the canister through concentrator outlet 130. In an embodiment, the vented gases may be directed through muffler 133 to reduce the noise produced by releasing the pressurized gas from the canister. As gas is released from canister 302, the pressure in the canister drops, allowing the nitrogen to become desorbed from the gas separation adsorbent. The released nitrogen exits the canister through outlet 130, resetting the canister to a state that allows renewed separation of oxygen from an air stream. Muffler 133 may include open cell foam (or another material) to muffle the sound of the gas leaving the oxygen concentrator. In some embodiments, the combined muffling components/techniques for the input of air and the output of gas, may provide for oxygen concentrator operation at a sound level below 50 decibels, for example.

During venting of the canisters, it is advantageous that at least a majority of the nitrogen is removed. In an embodiment, at least about 50%, at least about 60%, at least about 70%, at least about 80%, at least about 90%, at least about 95%, at least about 98%, or substantially all of the nitrogen in a canister is removed before the canister is re-used to separate oxygen from air. In some embodiments, a canister may be further purged of nitrogen using an oxygen enriched stream that is introduced into the canister from the other canister.

In an exemplary embodiment, a portion of the oxygen enriched gas may be transferred from canister 302 to canister 304 when canister 304 is being vented of nitrogen. Transfer of oxygen enriched gas from canister 302 to 304, during venting of canister 304, helps to further purge nitrogen (and other gases) from the canister. In an embodiment, oxygen enriched gas may travel through flow restrictors 151, 153, and 155 between the two canisters. Flow restrictor 151 may be a trickle flow restrictor. Flow restrictor 151, for example, may be a 0.009D flow restrictor (e.g., the flow restrictor has a radius 0.009" which is less than the diameter of the tube it is inside). Flow restrictors 153 and 155 may be 0.013D flow restrictors. Other flow restrictor types and sizes are also contemplated and may be used depending on the specific configuration and tubing used to couple the canisters. In some embodiments, the flow restrictors may be press fit flow restrictors that restrict air flow by introducing a narrower diameter in their respective tube. In some embodiments, the press fit flow restrictors may be made of sapphire, metal or plastic (other materials are also contemplated).

Flow of oxygen enriched gas is also controlled by use of valve 152 and valve 154. Valves 152 and 154 may be opened for a short duration during the venting process (and may be closed otherwise) to prevent excessive oxygen loss out of the purging canister. Other durations are also contemplated. In an exemplary embodiment, canister 302 is being vented and it is desirable to purge canister 302 by passing a portion of the oxygen enriched gas being produced in canister 304 into canister 302. A portion of oxygen enriched gas, upon pressurization of canister 304, will pass through flow restrictor 151 into canister 302 during venting of canister 302. Additional oxygen enriched gas is passed into canister 302, from canister 304, through valve 154 and flow restrictor 155. Valve 152 may remain closed during the transfer process, or may be opened if additional oxygen enriched gas is needed. The selection of appropriate flow restrictors 151 and 155, coupled with controlled opening of valve 154 allows a controlled amount of oxygen enriched gas to be sent from canister 304 to 302. In an embodiment, the controlled amount of oxygen enriched gas is an amount sufficient to purge canister 302 and minimize the loss of oxygen enriched gas through venting valve 132 of canister 302. While this embodiment describes venting of canister 302, it should be understood that the same process can be used to vent canister 304 using flow restrictor 151, valve 152 and flow restrictor 153.

The pair of equalization/vent valves 152/154 work with flow restrictors 153 and 155 to optimize the air flow balance between the two canisters. This may allow for better flow control for venting the canisters with oxygen enriched gas from the other of the canisters. It may also provide better flow direction between the two canisters. It has been found that, while flow valves 152/154 may be operated as bi-directional valves, the flow rate through such valves varies depending on the direction of fluid flowing through the valve. For example, oxygen enriched gas flowing from canister 304 toward canister 302 has a flow rate faster through valve 152 than the flow rate of oxygen enriched gas flowing from canister 302 toward canister 304 through valve 152. If a single valve was to be used, eventually either too much or too little oxygen enriched gas would be sent between the canisters and the canisters would, over time, begin to produce different amounts of oxygen enriched gas. Use of opposing valves and flow restrictors on parallel air pathways may equalize the flow pattern of the oxygen between the two canisters. Equalising the flow may allow for a steady amount of oxygen available to the user over multiple cycles and also may allow a predictable volume of oxygen to purge the other of the canisters. In some embodiments, the air pathway may not have restrictors but may instead have a valve with a built-in resistance or the air pathway itself may have a narrow radius to provide resistance.

At times, oxygen concentrator may be shut down for a period of time. When an oxygen concentrator is shut down, the temperature inside the canisters may drop as a result of the loss of adiabatic heat from the compression system. As the temperature drops, the volume occupied by the gases inside the canisters will drop. Cooling of the canisters may lead to a negative pressure in the canisters. Valves (e.g., valves 122, 124, 132, and 134) leading to and from the canisters are dynamically sealed rather than hermetically sealed. Thus, outside air may enter the canisters after shutdown to accommodate the pressure differential. When outside air enters the canisters, moisture from the outside air may condense inside the canister as the air cools. Condensation of water inside the canisters may lead to gradual degradation of the gas separation adsorbents, steadily reducing ability of the gas separation adsorbents to produce oxygen enriched gas.

In an embodiment, outside air may be inhibited from entering canisters after the oxygen concentrator is shutdown by pressurising both canisters prior to shutdown. By storing the canisters under a positive pressure, the valves may be forced into a hermetically closed position by the internal pressure of the air in the canisters. In an embodiment, the pressure in the canisters, at shutdown, should be at least greater than ambient pressure. As used herein the term "ambient pressure" refers to the pressure of the surroundings in which the oxygen concentrator is located (e.g. the pressure inside a room, outside, in a plane, etc.). In an embodiment, the pressure in the canisters, at shutdown, is at least greater than standard atmospheric pressure (i.e., greater than 760 mmHg (Torr), 1 atm, 101,325 Pa). In an embodiment, the pressure in the canisters, at shutdown, is at least about 1.1 times greater than ambient pressure; is at least about 1.5 times greater than ambient pressure; or is at least about 2 times greater than ambient pressure.

In an embodiment, pressurization of the canisters may be achieved by directing pressurized air into each canister from the compression system and closing all valves to trap the pressurized air in the canisters. In an exemplary embodiment, when a shutdown sequence is initiated, inlet valves 122 and 124 are opened and outlet valves 132 and 134 are closed. Because inlet valves 122 and 124 are joined together by a common conduit, both canisters 302 and 304 may become pressurized as air and or oxygen enriched gas from one canister may be transferred to the other canister. This situation may occur when the pathway between the compression system and the two inlet valves allows such transfer. Because the oxygen concentrator operates in an alternating pressurize/venting mode, at least one of the canisters should be in a pressurized state at any given time. In an alternate embodiment, the pressure may be increased in each canister by operation of compression system 200. When inlet valves 122 and 124 are opened, pressure between canisters 302 and 304 will equalize, however, the equalized pressure in either canister may not be sufficient to inhibit air from entering the canisters during shutdown. In order to ensure that air is inhibited from entering the canisters, compression system 200 may be operated for a time sufficient to increase the pressure inside both canisters to a level at least greater than ambient pressure. Regardless of the method of pressurization of the canisters, once the canisters are pressurized, inlet valves 122 and 124 are closed, trapping the pressurized air inside the canisters, which inhibits air from entering the canisters during the shutdown period.

Figure 2:
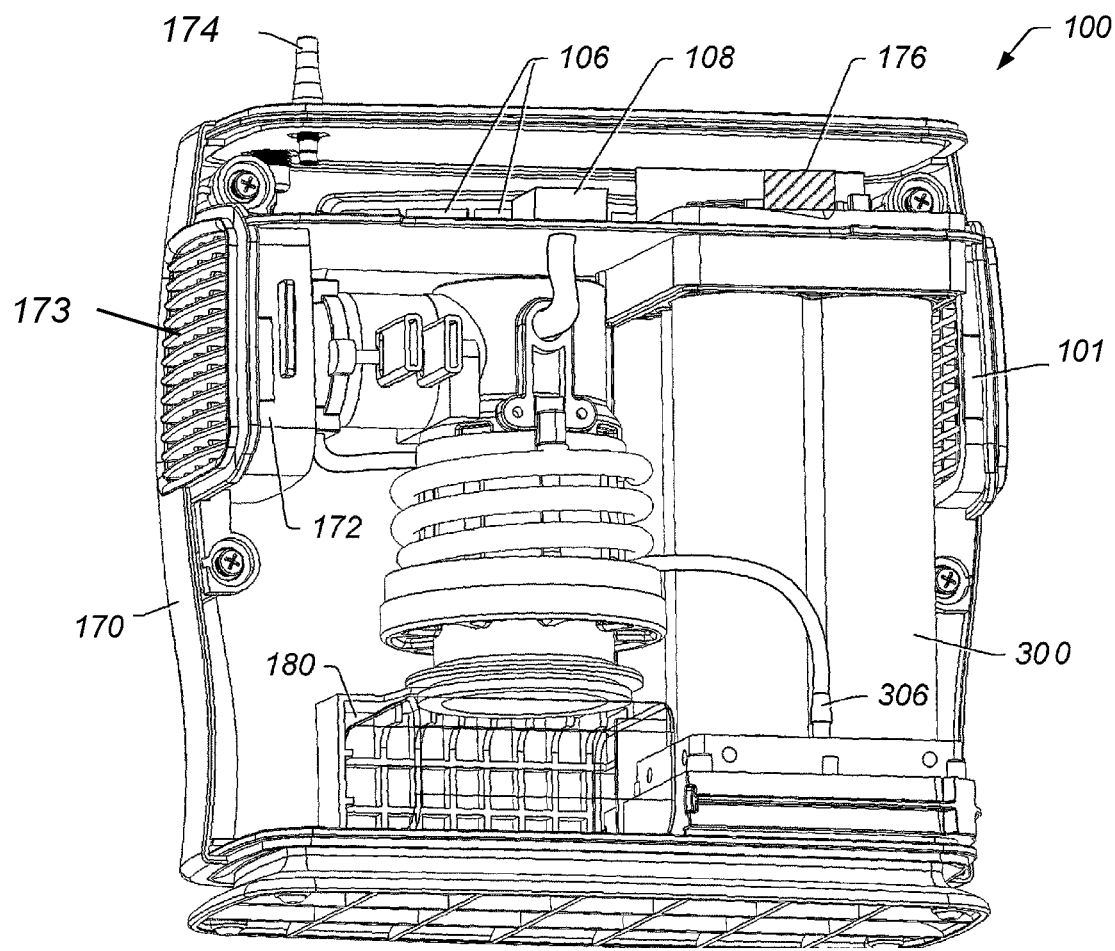
FIG. 2 depicts a side view of the main components of an oxygen concentrator.

Referring to FIG. 2, an embodiment of an oxygen concentrator 100 is depicted. Oxygen concentrator 100 includes a compression system 200, a canister assembly 300, and a power supply 180 disposed within an outer housing 170. Inlets 101 are located in outer housing 170 to allow air from the environment to enter oxygen concentrator 100. Inlets 101 may allow air to flow into the compartment to assist with cooling of the components in the compartment. Power supply 180 provides a source of power for the oxygen concentrator 100. Compression system 200 draws air in through the inlet 107 and muffler 108. Muffler 108 may reduce noise of air being drawn in by the compression system and also may include a desiccant material to remove water from the incoming air. Oxygen concentrator 100 may further include fan 172 used to vent air and other gases from the oxygen concentrator.

Compression System

Figure 3A:
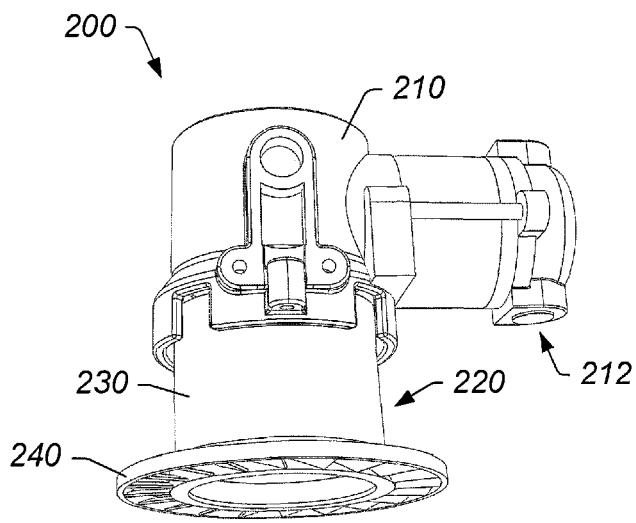
FIG. 3A depicts a perspective side view of a compression system.
Figure 3B:
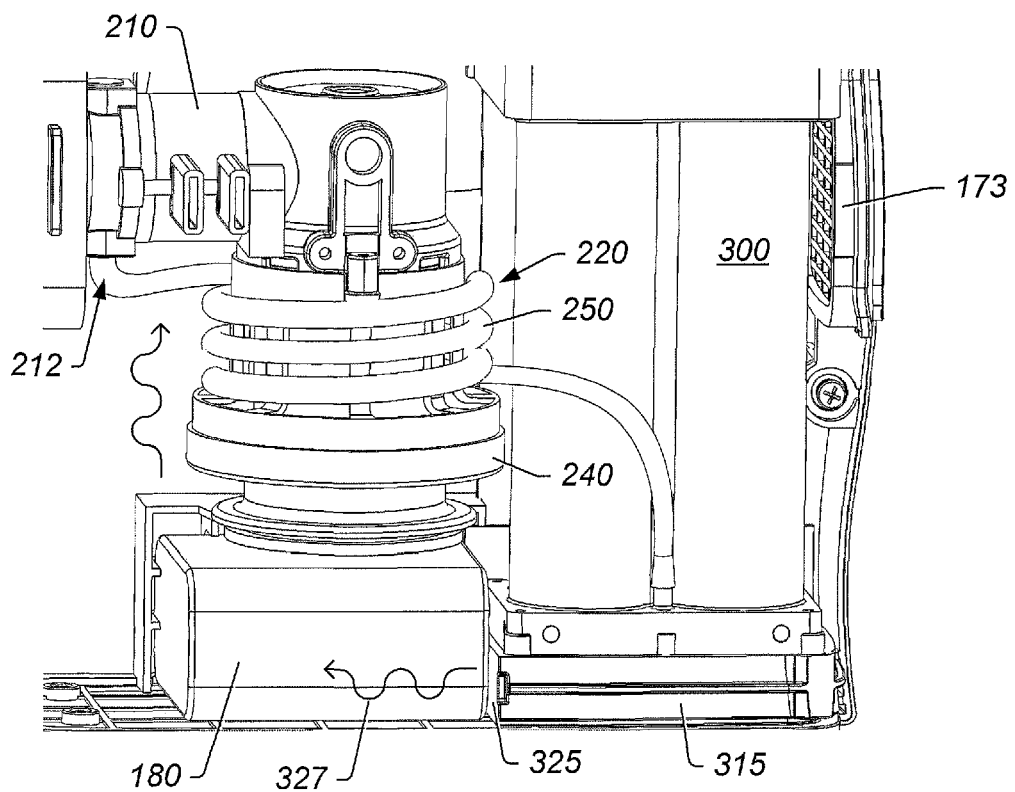
FIG. 3B depicts a side view of a compression system that includes a heat exchange conduit.

In some embodiments, compression system 200 includes one or more compressors. In another embodiment, compression system 200 includes a single compressor, coupled to all of the canisters of canister system 300. Turning to FIGS. 3A and 3B, a compression system 200 is depicted that includes compressor 210 and motor 220. Motor 220 is coupled to compressor 210 and provides an operating force to the compressor to operate the compression mechanism. For example, motor 220 may be a motor providing a rotating component that causes cyclical motion of a component of the compressor that compresses air. When compressor 210 is a piston type compressor, motor 220 provides an operating force which causes the piston of compressor 210 to be reciprocated. Reciprocation of the piston causes compressed air to be produced by compressor 210. The flow rate of the compressed air is, in part, estimated by the speed that the compressor is operated at, (e.g., how fast the piston is reciprocated). Motor 220, therefore, may be a variable speed motor that is operable at various speeds to dynamically control the flow rate of air produced by compressor 210.

In one embodiment, compressor 210 includes a single head wobble type compressor having a piston. Other types of compressors may be used such as diaphragm compressors and other types of piston compressors. Motor 220 may be a DC or AC motor and provides the operating power to the compressing component of compressor 210. Motor 220, in an embodiment, may be a brushless DC motor. Motor 220 may be a variable speed motor capable of operating the compressing component of compressor 210 at variable speeds. Motor 220 may be coupled to controller 400, as depicted in FIG. 1, which sends operating signals to the motor to control the operation of the motor. For example, controller 400 may send signals to motor 220 to: turn the motor on, turn motor the off, and set the operating speed of motor.

Compression system 200 inherently creates substantial heat. Heat is caused by the consumption of power by motor 220 and the conversion of power into mechanical motion. Compressor 210 generates heat due to the increased resistance to movement of the compressor components by the air being compressed. Heat is also inherently generated due to adiabatic compression of the air by compressor 210. Thus, the continual pressurization of air produces heat in the enclosure. Additionally, power supply 180 may produce heat as power is supplied to compression system 200. Furthermore, users of the oxygen concentrator may operate the device in unconditioned environments (e.g., outdoors) at potentially higher ambient temperatures than indoors, thus the incoming air will already be in a heated state.

Heat produced inside oxygen concentrator 100 can be problematic. Lithium ion batteries are generally employed as a power source for oxygen concentrators due to their long life and light weight. Lithium ion battery packs, however, are dangerous at elevated temperatures and safety controls are employed in oxygen concentrator 100 to shutdown the system if dangerously high power supply temperatures are detected. Additionally, as the internal temperature of oxygen concentrator 100 increases, the amount of oxygen generated by the concentrator may decrease. This is due, in part, to the decreasing amount of oxygen in a given volume of air at higher temperatures. If the amount of produced oxygen drops below a predetermined amount, the oxygen concentrator 100 may automatically shut down, or sound an alarm.

Because of the compact nature of oxygen concentrators, dissipation of heat can be difficult. Solutions typically involve the use of one or more fans to create a flow of cooling air through the enclosure. Such solutions, however, require additional power from the power supply and thus shorten the portable usage time of the oxygen concentrator. In an embodiment, a passive cooling system may be used that takes advantage of the mechanical power produced by motor of the compressor 210. Referring to FIGS. 3A and 3B, compression system 200 includes motor 220 having an external rotating armature 230. Specifically, armature 230 of motor 220 (e.g. a DC motor) is wrapped around the stationary field that is driving the armature. Since motor 220 is a large contributor of heat to the overall system it is helpful to pull heat off of the motor and sweep it out of the enclosure. With the external high speed rotation, the relative velocity of the major component of the motor and the air in which it exists is very high. The surface area of the armature is larger if externally mounted than if it is internally mounted. Since the rate of heat exchange is proportional to the surface area and the square of the velocity, using a larger surface area armature mounted externally increases the ability of heat to be dissipated from motor 220. The gain in cooling efficiency by mounting the armature externally, allows the elimination of one or more cooling fans, thus reducing the weight and power consumption while maintaining the interior of the oxygen concentrator within the appropriate temperature range. Additionally, the rotation of the externally mounted armature creates movement of air proximate to the motor to create additional cooling.

Moreover, an external rotating armature may help the efficiency of the motor, allowing less heat to be generated. A motor having an external armature operates similar to the way a flywheel works in an internal combustion engine. When the motor is driving the compressor, the resistance to rotation is low at low pressures. When the pressure of the compressed air is higher, the resistance to rotation of the motor is higher. As a result, the motor does not maintain consistent ideal rotational stability, but instead surges and slows down depending on the pressure demands of the compressor. This tendency of the motor to surge and then slow down is inefficient and therefore generates heat. Use of an external armature adds greater angular momentum to the motor which helps to compensate for the variable resistance experienced by the motor. Since the motor does not have to work as hard, the heat produced by the motor may be reduced.

In an embodiment, cooling efficiency may be further increased by coupling an air transfer device 240 to external rotating armature 230. In an embodiment, air transfer device 240 is coupled to the external armature 230 such that rotation of the external armature causes the air transfer device to create an airflow that passes over at least a portion of the motor. In an embodiment, air transfer device includes one or more fan blades coupled to the armature. In an embodiment, a plurality of fan blades may be arranged in an annular ring such that the air transfer device acts as an impeller that is rotated by movement of the external rotating armature. As depicted in FIGS. 3A and 3B, air transfer device 240 may be mounted to an outer surface of the external armature 230, in alignment with the motor. The mounting of the air transfer device to the armature allows airflow to be directed toward the main portion of the external rotating armature, providing a cooling effect during use. In an embodiment, the air transfer device directs air flow such that a majority of the external rotating armature is in the air flow path.

Further, referring to FIGS. 3A and 3B, air pressurized by compressor 210 exits compressor 210 at compressor outlet 212. A compressor outlet conduit 250 is coupled to compressor outlet 212 to transfer the compressed air to canister system 300. As noted previously, compression of air causes an increase in the temperature of the air. This increase in temperature can be detrimental to the efficiency of the oxygen concentrator. In order to reduce the temperature of the pressurized air, compressor outlet conduit 250 is placed in the air flow path produced by air transfer device 240. At least a portion of compressor outlet conduit 250 may be positioned proximate to motor 220. Thus, airflow, created by air transfer device, may contact both motor 220 and compressor outlet conduit 250. In one embodiment, a majority of compressor outlet conduit 250 is positioned proximate to motor 220. In an embodiment, the compressor outlet conduit 250 is coiled around motor 220, as depicted in FIG. 3B.

In an embodiment, the compressor outlet conduit 250 is composed of a heat exchange metal. Heat exchange metals include, but are not limited to, aluminum, carbon steel, stainless steel, titanium, copper, copper-nickel alloys or other alloys formed from combinations of these metals. Thus, compressor outlet conduit 250 can act as a heat exchanger to remove heat that is inherently caused by compression of the air. By removing heat from the compressed air, the number of molecules in a given volume at a given pressure is increased. As a result, the amount of oxygen that can be generated by each canister during each pressure swing cycle may be increased.

The heat dissipation mechanisms described herein are either passive or make use of elements required for the oxygen concentrator 100. Thus, for example, dissipation of heat may be increased without using systems that require additional power. By not requiring additional power, the run-time of the battery packs may be increased and the size and weight of the oxygen concentrator may be minimized. Likewise, use of an additional box fan or cooling unit may be eliminated Eliminating such additional features reduces the weight and power consumption of the oxygen concentrator.

As discussed above, adiabatic compression of air causes the air temperature to increase. During venting of a canister in canister system 300, the pressure of the gas being released from the canisters decreases. The adiabatic decompression of the gas in the canister causes the temperature of the gas to drop as it is vented. In an embodiment, the cooled vented gases from canister system 300 are directed toward power supply 180 and toward compression system 200. In an embodiment, base 315 of compression system 200 receives the vented gases from the canisters. The vented gases 327 are directed through base 315 toward outlet 325 of the base and toward power supply 180. The vented gases, as noted, are cooled due to decompression of the gases and therefore passively provide cooling to the power supply. When the compression system is operated, the air transfer device will gather the cooled vented gases and direct the gases toward the motor of compression system 200. Fan 172 may also assist in directing the vented gas across compression system 200 and out of the housing 170. In this manner, additional cooling may be obtained without requiring any further power requirements from the battery.

Outlet System

An outlet system, coupled to one or more of the canisters, includes one or more conduits for providing oxygen enriched gas to a user. In an embodiment, oxygen enriched gas produced in either of canisters 302 and 304 is collected in accumulator 106 through check valves 142 and 144, respectively, as depicted schematically in FIG. 1. The oxygen enriched gas leaving the canisters may be collected in an oxygen accumulator 106 prior to being provided to a user. In some embodiments, a tube may be coupled to the accumulator 106 to provide the oxygen enriched gas to the user. Oxygen enriched gas may be provided to the user through an airway delivery device that transfers the oxygen enriched gas to the user's mouth and/or nose. In an embodiment, an outlet may include a tube that directs the oxygen toward a user's nose and/or mouth that may not be directly coupled to the user's nose.

Figure 4A:
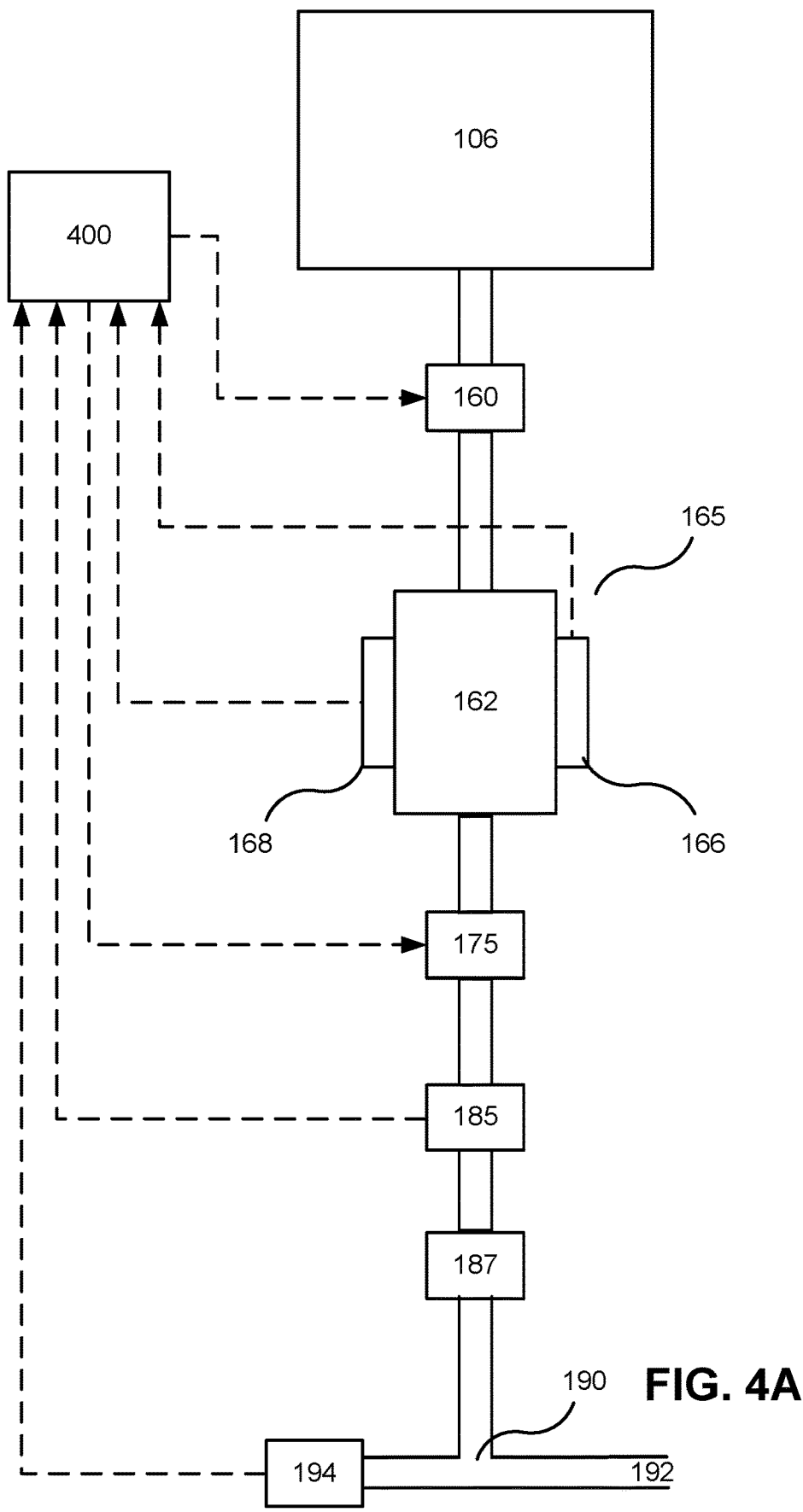
FIG. 4A depicts a schematic diagram of the outlet components of an oxygen concentrator.

Turning to FIG. 4A, a schematic diagram of an embodiment of an outlet system for an oxygen concentrator is shown. A supply valve 160 may be coupled to an outlet tube to control the release of the oxygen enriched gas from accumulator 106 to expansion chamber 162. In an embodiment, supply valve 160 is an electromagnetically actuated plunger valve. Supply valve 160 is actuated by controller 400 to control the release of oxygen enriched gas to expansion chamber 162. Supply valve 160 is generally open by default except as described below. In an alternative embodiment, accumulator 106 is combined with expansion chamber 162 and the supply valve 160 is positioned upstream of the combined chamber.

Oxygen enriched gas in accumulator 106 passes through supply valve 160 into expansion chamber 162 as depicted in FIG. 4A. In an embodiment, expansion chamber 162 may include one or more devices for determining an oxygen concentration of gas passing through the chamber. Oxygen enriched gas in expansion chamber 162 builds through release of gas from accumulator 106 by supply valve 160, and is then released from the expansion chamber 162 via a control valve 175, a mass flow sensor 185 and a particulate filter 187.

Actuation of control valve 175 is not timed or synchronized to the pressure swing adsorption process. Instead, actuation of control valve 175 is, in some embodiments, synchronized to the user's breathing. Additionally, control valve 175 may have continuously-valued actuation to establish a clinically effective amplitude profile for the bolus of oxygen enriched gas.

Mass flow sensor 185 may be any sensor capable of estimating the mass flow rate of gas flowing through the conduit. Particulate filter 187 may filter bacteria, dust, granule particles, etc. prior to delivery of the oxygen enriched gas to the user. The oxygen enriched gas passes through filter 187 to connector 190 which sends the oxygen enriched gas to the user via conduit 192 and to pressure sensor 194.

The fluid dynamics of the outlet pathway, coupled with the programmed actuations of control valve 175, may result in a bolus of oxygen being delivered at the correct time and with an amplitude profile that assures rapid delivery into the user's lungs without any excessive flow rates that would result in retrograde flow waste. If the bolus can be delivered in this manner, there may be a linear relationship between the prescribed continuous flow rate and the therapeutically equivalent bolus volume required in pulsed delivery mode for a user at rest with a given breath pattern. For example, the total volume of the bolus required to emulate continuous-flow prescriptions may be equal to 11 mL for each LPM of prescribed continuous flow rate, i.e., 11 mL for a prescription of 1 LPM; 22 mL for a prescription of 2 LPM; 33 mL for a prescription of 3 LPM; 44 mL for a prescription of 4 LPM; 55 mL for a prescription of 5 LPM; etc. This amount is generally referred to as the LPM equivalent bolus volume. It should be understood that the LPM equivalent may vary between oxygen concentrators due to differences in construction design, tubing size, chamber size, etc. The LPM equivalent will also vary depending on the user's breath pattern.

Expansion chamber 162 may include oxygen sensing apparatus for determining an oxygen concentration of gas passing through the chamber. In an embodiment, the oxygen concentration of gas passing through expansion chamber 162 is estimated using an oxygen sensor 165. In some versions, the oxygen sensor 165 may be implemented by a set of sensors. For example, in some cases, the oxygen sensor may be implemented with any of one, more, or all of a pressure sensor 166, a temperature sensor 168, and mass flow sensor 185. Various implementations of the oxygen sensor 165 are described in detail below.

Mass flow sensor 185 may be used to measure the mass flow rate of gas flowing through the outlet system. Mass flow sensor 185 may be coupled to controller 400. The mass flow rate of gas flowing through the outlet system may be an indication of the breathing volume of the user. Changes in the mass flow rate of gas flowing through the outlet system may also be used to determine a breathing rate of the user. Controller 400 may control actuation of control valve 175 based on the breathing rate and/or breathing volume of the user, as estimated by mass flow sensor 185.

Oxygen enriched gas passes through mass flow sensor 185 to filter 187. Filter 187 removes bacteria, dust, granule particles, etc. prior to providing the oxygen enriched gas to the user. The filtered oxygen enriched gas passes through filter 187 to connector 190. Connector 190 may be a "Y" connector coupling the outlet of filter 187 to pressure sensor 194 and outlet conduit 192. Pressure sensor 194 may be used to monitor the pressure of the gas passing through conduit 192 to the user. Changes in pressure, sensed by pressure sensor 194, may be used to determine the onset(s) of inhalation (also referred to as trigger instant(s)). Hence a pressure signal from such a pressure sensor may represent a breathing rate of the user. Controller 400 may control actuation of control valve 175 based on the breathing rate and/or onset of inhalation of the user, as estimated by pressure sensor 194. In an embodiment, controller 400 may control actuation of control valve 175 based on information provided by oxygen sensor 165, mass flow sensor 185, and pressure sensor 194.

Figure 4B:
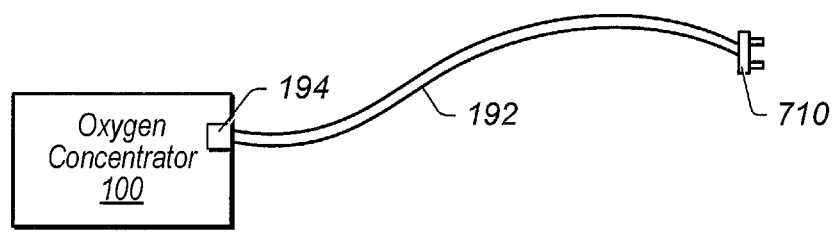
FIG. 4B depicts an outlet conduit for an oxygen concentrator.
Figure 4C:
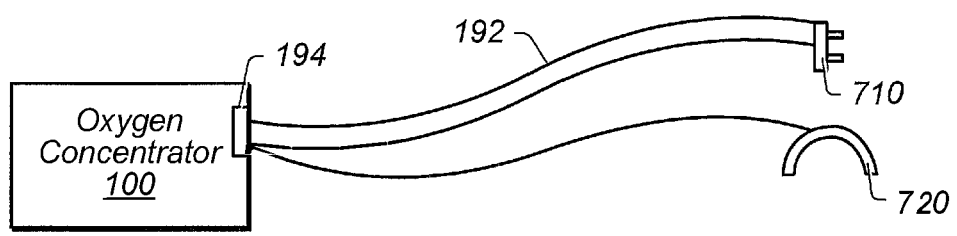
FIG. 4C depicts an alternate outlet conduit for an oxygen concentrator.

Oxygen enriched gas may be provided to a user through conduit 192. In an embodiment, conduit 192 may be a silicone tube. Conduit 192 may be coupled to a user using an airway coupling member (e.g., airway delivery device 710), as depicted in FIGS. 4B and 4C. Airway delivery device 710 may be any device capable of providing the oxygen enriched gas to nasal cavities or oral cavities. Examples of airway coupling members include, but are not limited to: nasal masks, nasal pillows, nasal prongs, nasal cannulas, and mouthpieces. A nasal cannula airway delivery device is depicted in FIG. 4B. During use, oxygen enriched gas from oxygen concentrator 100 is provided to the user through conduit 192 and airway coupling member (e.g., airway delivery device 710). Airway delivery device 710 is positioned proximate to a user's airway (e.g., proximate to the user's mouth and or nose) to allow delivery of the oxygen enriched gas to the user while allowing the user to breathe air from the surroundings.

In an alternate embodiment, a mouthpiece may be used to provide oxygen enriched gas to the user. As shown in FIG. 4C, a mouthpiece 720 may be coupled to oxygen concentrator 100. Mouthpiece 720 may be the only device used to provide oxygen enriched gas to the user, or a mouthpiece may be used in combination with a nasal delivery device (e.g., a nasal cannula). As depicted in FIG. 4C, oxygen enriched gas may be provided to a user through both a nasal coupling member (e.g., airway delivery device 710) and a mouthpiece 720.

Mouthpiece 720 is removably positionable in a user's mouth. In one embodiment, mouthpiece 720 is removably couplable to one or more teeth in a user's mouth. During use, oxygen enriched gas is directed into the user's mouth via the mouthpiece. Mouthpiece 720 may be a night guard mouthpiece which is molded to conform to the user's teeth. Alternatively, mouthpiece may be a mandibular repositioning device. In an embodiment, at least a majority of the mouthpiece is positioned in a user's mouth during use.

During use, oxygen enriched gas may be directed to mouthpiece 720 when a change in pressure is detected proximate to the mouthpiece. In one embodiment, mouthpiece 720 may be coupled to a pressure sensor. When a user inhales air through the user's mouth, pressure sensor 194 may detect a drop in pressure proximate to the mouthpiece. Controller 400 of oxygen concentrator 100 may deliver a bolus of oxygen enriched gas to the user at the onset of inhalation.

During typical breathing of an individual, inhalation may occur through the nose, through the mouth or through both the nose and the mouth. Furthermore, breathing may change from one passageway to another depending on a variety of factors. For example, during more active activities, a user may switch from breathing through their nose to breathing through their mouth, or breathing through their mouth and nose. A system that relies on a single mode of delivery (either nasal or oral), may not function properly if breathing through the monitored pathway is stopped. For example, if a nasal cannula is used to provide oxygen enriched gas to the user, an inhalation sensor (e.g., a pressure sensor or flow rate sensor) may be coupled to the nasal cannula to determine the onset of inhalation. If the user stops breathing through their nose, and switches to breathing through their mouth, the oxygen concentrator 100 may not know when to provide the oxygen enriched gas since there is no feedback from the nasal cannula. Under such circumstances, oxygen concentrator 100 may increase the flow rate and/or increase the frequency of providing oxygen enriched gas until the inhalation sensor detects an inhalation by the user. If the user switches between breathing modes often, the default mode of providing oxygen enriched gas may cause the oxygen concentrator 100 to work harder, potentially limiting the portable usage time of the system.

In an embodiment, a mouthpiece 720 is used in combination with an airway delivery device 710 (e.g., a nasal cannula) to provide oxygen enriched gas to a user, as depicted in FIG. 4C. Both mouthpiece 720 and airway delivery device 710 are coupled to an inhalation sensor. In one embodiment, mouthpiece 720 and airway delivery device 710 are coupled to the same inhalation sensor. In an alternate embodiment, mouthpiece 720 and airway delivery device 710 are coupled to different inhalation sensors. In either embodiment, inhalation sensor(s) may now detect the onset of inhalation from either the mouth or the nose. Oxygen concentrator 100 may be configured to provide oxygen enriched gas to the device (i.e. mouthpiece 720 or airway delivery device 710) proximate to which the onset of inhalation was detected. Alternatively, oxygen enriched gas may be provided to both mouthpiece 720 and the airway delivery device 710 if onset of inhalation is detected proximate either device. The use of a dual delivery system, such as depicted in FIG. 4C may be particularly useful for users when they are sleeping and may switch between nose breathing and mouth breathing without conscious effort.

Controller System

Operation of oxygen concentrator 100 may be performed automatically using an internal controller 400 coupled to various components of the oxygen concentrator 100, as described herein. Controller 400 includes one or more processors 410 and internal memory 420, as depicted in FIG. 1. Methods used to operate and monitor oxygen concentrator 100 may be implemented by program instructions stored in memory 420 or a carrier medium coupled to controller 400, and executed by one or more processors 410. A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, flash memory, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, controller 400 includes processor 410 that includes, for example, one or more field programmable gate arrays (FPGAs), microcontrollers, etc. included on a circuit board disposed in oxygen concentrator 100. Processor 410 is capable of executing programming instructions stored in memory 420. In some embodiments, programming instructions may be built into processor 410 such that a memory external to the processor may not be separately accessed (i.e., the memory 420 may be internal to the processor 410).

Processor 410 may be coupled to various components of oxygen concentrator 100, including, but not limited to compression system 200, one or more of the valves used to control fluid flow through the system (e.g., valves 122, 124, 132, 134, 152, 154, 160, 175), oxygen sensor 165, pressure sensors 166, 194, mass flow sensor 185, temperature sensor 168, fans, and any other component that may be electrically controlled or monitored. In some embodiments, a separate processor (and/or memory) may be coupled to one or more of the components. Controller 400 is programmed to operate oxygen concentrator 100 and is further programmed to monitor the oxygen concentrator 100 for malfunction states. For example, in one embodiment, controller 400 is programmed to trigger an alarm if the system is operating and no breathing is detected by the user for a predetermined amount of time. For example, if controller 400 does not detect a breath for a period of 75 seconds, an alarm LED may be lit and/or an audible alarm may be sounded. If the user has truly stopped breathing, for example, during a sleep apnea episode, the alarm may be sufficient to awaken the user, causing the user to resume breathing. The action of breathing may be sufficient for controller 400 to reset this alarm function. Alternatively, if the system is accidently left on when output conduit 192 is removed from the user, the alarm may serve as a reminder for the user to turn oxygen concentrator 100 off.

Controller 400 is further coupled to oxygen sensor 165, and may be programmed for continuous or periodic monitoring of the oxygen concentration of the oxygen enriched gas passing through expansion chamber 162. A minimum oxygen concentration threshold may be programmed into controller 400, such that the controller lights an LED visual alarm and/or an audible alarm to warn the user of the low concentration of oxygen.

Controller 400 is also coupled to internal power supply 180 and is capable of monitoring the level of charge of the internal power supply. A minimum voltage and/or current threshold may be programmed into controller 400, such that the controller lights an LED visual alarm and/or an audible alarm to warn the user of low power condition. The alarms may be activated intermittently and at an increasing frequency as the battery approaches zero usable charge.

Further functions of controller 400 are described in detail in other sections of this disclosure.

Outer Housing—Control Panel

Figure 5:
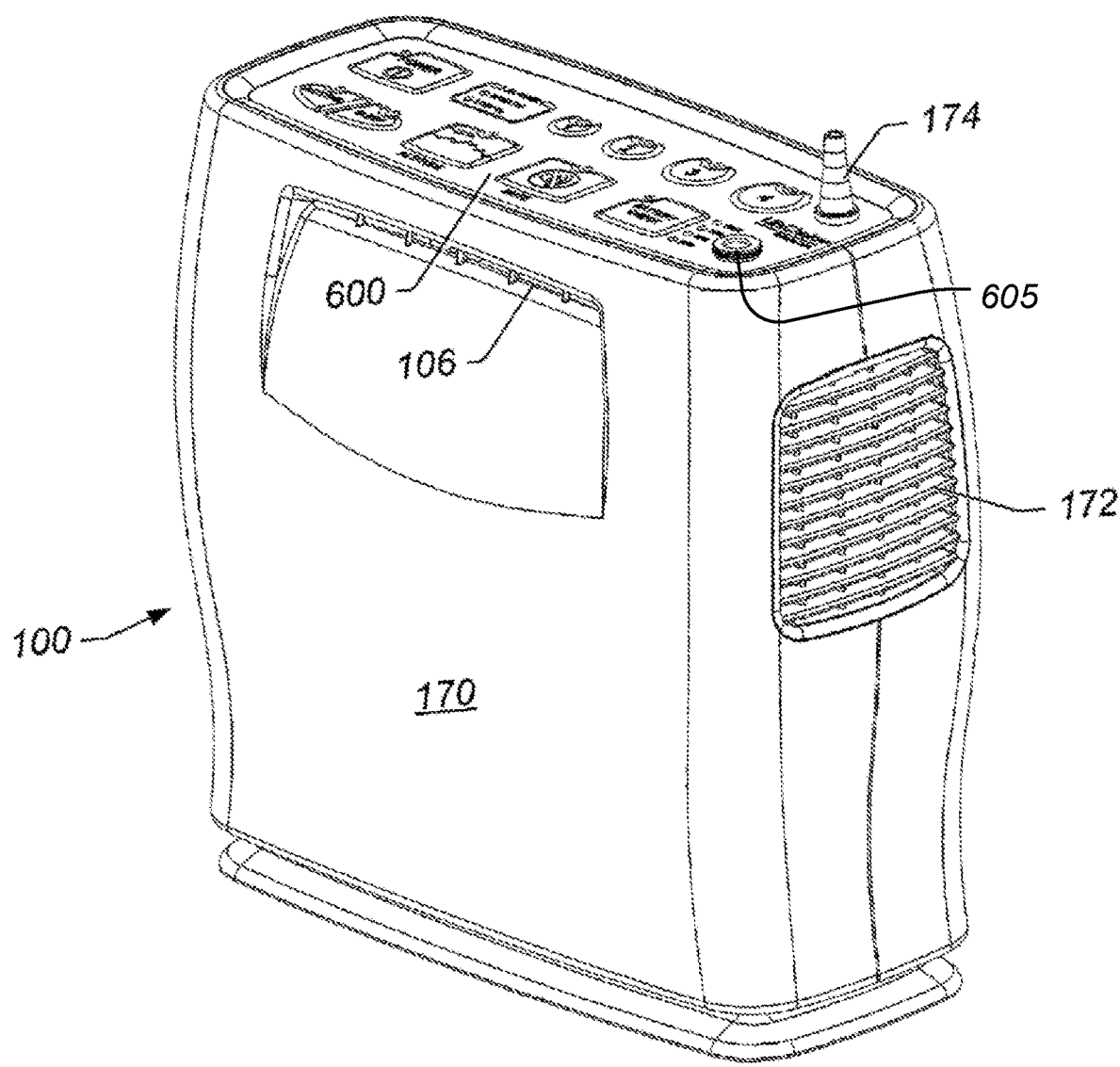
FIG. 5 depicts an outer housing for an oxygen concentrator.

FIG. 5 depicts an embodiment of an outer housing 170 of an oxygen concentrator 100. In some embodiments, outer housing 170 may be comprised of a light-weight plastic. Outer housing includes compression system inlets 107, cooling system passive inlet 101 and outlet 173 at either end of outer housing 170, outlet port 174, and control panel 600. Inlet 101 and outlet 173 allow cooling air to enter the housing, flow through the housing, and exit the interior of housing 170 to aid in cooling of the oxygen concentrator 100. Compression system inlets 107 allow air to enter the compression system. Outlet port 174 is used to attach a conduit to provide oxygen enriched gas produced by the oxygen concentrator 100 to a user.

Figure 6:
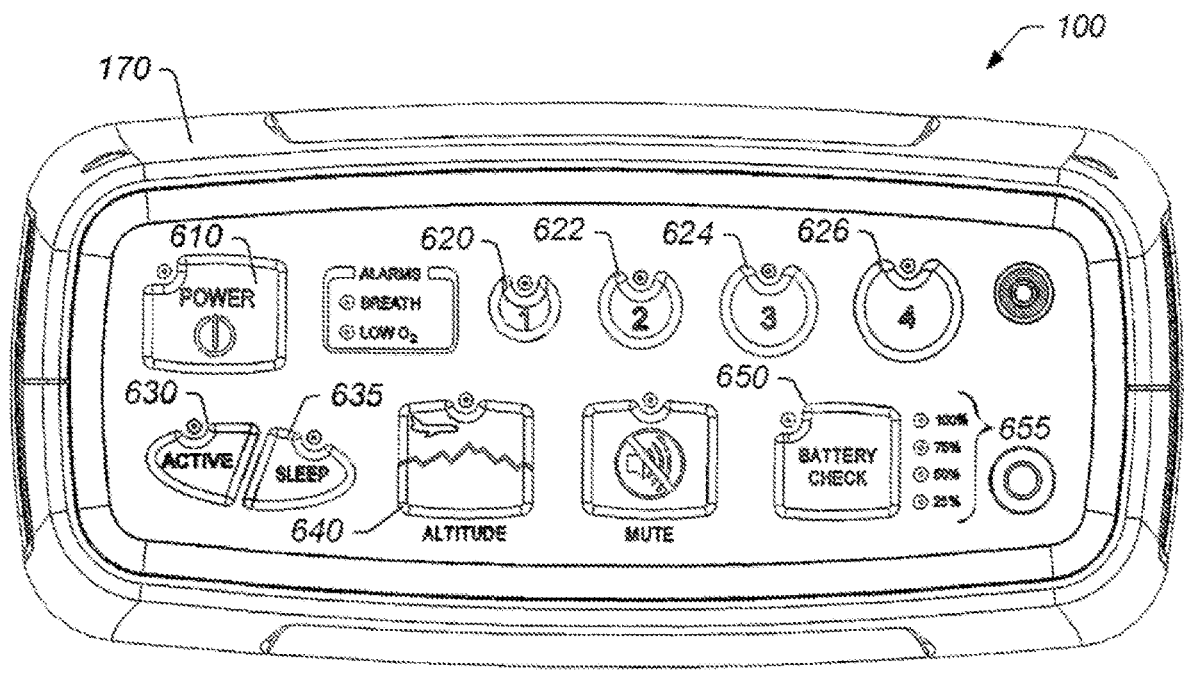
FIG. 6 depicts a control panel for an oxygen concentrator.

Control panel 600 serves as an interface between a user and controller 400 to allow the user to initiate predetermined operation modes of the oxygen concentrator 100 and to monitor the status of the system. Charging input port 605 may be disposed in control panel 600. FIG. 6 depicts an embodiment of control panel 600.

In some embodiments, control panel 600 may include buttons to activate various operation modes for the oxygen concentrator 100. For example, control panel may include power button 610, dosage buttons 620 to 626, active mode button 630, sleep mode button 635, and a battery check button 650. In some embodiments, one or more of the buttons may have a respective LED that may illuminate when the respective button is pressed (and may power off when the respective button is pressed again). Power button 610 may power the system on or off. If the power button is activated to turn the system off, controller 400 may initiate a shutdown sequence to place the system in a shutdown state (e.g., a state in which both canisters are pressurized). Dosage buttons 620, 622, 624, and 626 allow the prescribed continuous flow rate of oxygen enriched gas to be selected (e.g., 1 LPM by button 620, 2 LPM by button 622, 3 LPM by button 624, and 4 LPM by button 626). Altitude button 640 may be selected when a user is going to be in a location at a higher elevation than the oxygen concentrator 100 is regularly used by the user. The adjustments made by the oxygen concentrator 100 in response to activating altitude mode are described in more detail herein.

Battery check button 650 initiates a battery check routine in the oxygen concentrator 100 which results in a relative battery power remaining LED 655 being illuminated on control panel 600.

A user may have a low breathing rate or depth if relatively inactive (e.g., asleep, sitting, etc.) as estimated by comparing the detected breathing rate or depth to a threshold. The user may have a high breathing rate or depth if relatively active (e.g., walking, exercising, etc.). An active/sleep mode may be estimated automatically and/or the user may manually indicate a respective active or sleep mode by pressing button 630 for active mode and button 635 for sleep mode. The adjustments made by the oxygen concentrator 100 in response to activating active mode or sleep mode are described in more detail herein.

Methods of Delivery of Oxygen Enriched Gas

The main use of an oxygen concentrator 100 is to provide supplemental oxygen to a user. Generally, the flow rate of supplemental oxygen to be provided is estimated by a physician. Typical prescribed continuous flow rates of supplemental oxygen may range from about 1 LPM to up to about 10 LPM. The most commonly prescribed continuous flow rates are 1 LPM, 2 LPM, 3 LPM, and 4 LPM. Generally in a pulsed oxygen device, oxygen enriched gas is provided to the user in synchrony with the breathing cycle to emulate the continuous flow rate prescribed for the user. As used herein the term "breathing cycle" refers to an inhalation followed by an exhalation.

In order to minimize the amount of oxygen enriched gas that is needed to be produced to emulate the prescribed continuous flow rate, controller 400 may be programmed to time delivery of the oxygen enriched gas with the user's inhalations, a mode known as pulsed oxygen delivery (POD) or demand oxygen delivery. Releasing the oxygen enriched gas to the user as the user inhales may prevent unnecessary oxygen generation (further reducing power requirements) by not releasing oxygen, for example, when the user is exhaling. Reducing the amount of oxygen required may effectively reduce the amount of air compressing needed for oxygen concentrator 100 (and subsequently may reduce the power demand from the compressors).

Oxygen enriched gas produced by oxygen concentrator 100 is stored in an oxygen accumulator 106 and released to the user as the user inhales. The amount of oxygen enriched gas provided by the oxygen concentrator 100 is controlled, in part, by control valve 175. In an embodiment, control valve 175 is opened for a sufficient amount of time to provide the appropriate amount of oxygen enriched gas, as estimated by controller 400, to the user. In order to minimize the amount of oxygen required to emulate the prescribed continuous flow rate of a user, the oxygen enriched gas may be delivered as a bolus when a user's inhalation is first detected. For example, the bolus of oxygen enriched gas may be delivered in the first few milliseconds of a user's inhalation.

In an embodiment, pressure sensor 194 may be used to determine the onset of inhalation by the user. In use, a conduit for providing oxygen enriched gas is coupled to a user's nose and/or mouth through the airway delivery device 710 and/or 720. At the onset of an inhalation, the user begins to draw air into their body through the nose and/or mouth. As the air is drawn in, a negative pressure is generated at the end of the conduit, due, in part, to the venturi action of the air being drawn across the end of the delivery conduit. Such a drop in pressure may be detected in the signal provided by the pressure sensor 194 or other suitable sensor, to indicate the onset of inhalation. Upon detection of the onset of inhalation, control valve 175 is opened to deliver a bolus of oxygen enriched gas from the accumulator 106. A positive change or rise in the pressure indicates an exhalation by the user and is generally a time that release of oxygen enriched gas is discontinued. Generally, when a positive pressure change is sensed, control valve 175 is closed until the next onset of inhalation. Alternatively, control valve 175 may be closed after a predetermined interval known as the bolus duration. By measuring the intervals between adjacent onsets of inhalation, the user's breathing rate may be estimated. By measuring the intervals between onsets of inhalation and the following onsets of exhalation, the user's inspiratory time may be estimated.

Oxygen Sensor Based on Universal Gas Equation

One form of the Ideal or Universal Gas Equation or Law is $$PV = nRT \qquad (1)$$

where P is the (absolute) pressure of a gas in a vessel, V is the volume of the vessel, T is the (absolute) temperature of the gas in the vessel, n is the amount of gas (number of moles) in the vessel, and R is the universal gas constant, equal to 8.31 in SI units. Equation (1) holds regardless of the composition of the gas in the vessel.

An alternative form of the Ideal Gas Law is $$PV = mR_sT \qquad (2)$$

where m is the mass of gas in the vessel and $R_s$ is the specific gas constant of the gas in the vessel, defined as 1000 times the universal gas constant divided by the molecular mass of the gas in atomic mass units. For example, for nitrogen, $R_s$ is equal to 296.8; for oxygen, $R_s$ is equal to 259.8; and for argon, $R_s$ is equal to 208.0. When the gas in the vessel is a mixture of pure gases, the specific gas constant of the gas in the vessel is a function of the specific gas constants of the constituent gases in the mixture and their relative concentrations. In one formulation, the specific gas constant of the mixture is a weighted average of the specific gas constants of the gases in the mixture, weighted by their concentrations. That is, for a mixture of N gases, $$R_s = \sum_{i=1}^{N} C_i R_{si} \qquad (3)$$

where the $C_i$ are the fractional concentrations of the gases in the mixture (which must add to one) and the $R_{si}$ are their respective specific gas constants. For example, for dry, fresh air, whose nitrogen concentration $C_1$ may be approximated as 78%, oxygen concentration $C_2$ as 21%, and argon concentration $C_3$ as 1%, the specific gas constant $R_s$ is equal to 288.14.

In an alternative formulation, the reciprocal of the specific gas constant of the mixture is a weighted average of the reciprocals of the specific gas constants of the gases in the mixture, weighted by their concentrations. That is, $$\frac{1}{R_s} = \sum_{i=1}^{N} \frac{C_i}{R_{si}} \qquad (4)$$

Using this "reciprocal" formulation, the specific gas constant $R_s$ of dry, fresh air is equal to 287.0.

If the gas mixture is an "enriched" mixture, i.e. a known (un-enriched) mixture from which an unknown amount of one gas has been removed (e.g. oxygen enriched gas, which is air from which nitrogen has been removed by oxygen concentration), the concentrations become $BC_1$ (for the removed gas) and $EC_i$ (for the non-removed gas(es)), where B is the fraction of the original concentration of the removed gas remaining in the enriched mixture. Since the enriched concentrations must still add to one, it may be shown that the removal fraction B is $$B = \frac{1 - E \sum_{i=2}^{N} C_i}{C_1} \qquad (5)$$

Using the formulation of equation (3), the specific gas constant $R_s$ of the enriched gas is therefore given by $$R_s = BC_1 R_{s1} + E \sum_{i=2}^{N} C_i R_{si} = E \sum_{i=2}^{N} C_i(R_{si} - R_{s1}) + R_{s1} \qquad (6)$$

Equation (6) allows the concentration $EC_i$ of any non-removed gas in the enriched mixture to be derived from an estimate of the specific gas constant $R_s$ of the enriched mixture as follows:

$$EC_i = KC_i(R_{s1} - R_s) \qquad (7)$$

where the constant K may be precalculated from the (known) starting concentrations $C_i$ and specific gas constants $R_{si}$ as $$K = \frac{1}{\sum_{i=2}^{N} C_i(R_{s1} - R_{si})} \qquad (8)$$

If the concentrations $EC_i$ of the non-removed gas in the enriched mixture are determined using equation (7) for all i from 2 to N, the concentration $BC_1$ of the removed gas in the enriched mixture may be estimated using equation (5).

Note that if the mixture contains only two gases (N=2), the concentration of the non-removed gas (i=2) may be computed from equation (7) as $$EC_2 = \frac{R_{s1} - R_s}{R_{s1} - R_{s2}} \qquad (9)$$

which is independent of the starting concentrations $C_i$. Therefore, the present technology is applicable to general two-gas mixtures in which the concentrations are unknown, as well as enriched mixtures of three or more gases in which the starting (un-enriched) concentrations are known.

From Equation (2), if pressure P, volume V, temperature T, and mass m of the gas in a vessel are known, the specific gas constant $R_s$ of the gas may be derived as $$R_s = \frac{PV}{mT} \qquad (10)$$

It is difficult to measure the mass m of gas in a vessel such as the chamber 162. The mass flow sensor 185, however, can provide a signal representing the mass flow rate $\dot{m}(t)$ (rate of mass passing the sensor) of some portion of the gas as it leaves or enters the chamber 162. The measured mass flow rate $\dot{m}(t)$ may be integrated between times $t_1$ and $t_2$ to give the change in mass $\Delta m$ in the chamber 162 between $t_1$ and $t_2$:

$$\Delta m = \int_{t_1}^{t_2} \dot{m}(t) dt \qquad (11)$$

Pressure and temperature may be measured by the pressure sensor 166 and the temperature sensor 168 respectively at times $t_1$ and $t_2$, giving values $P_1$ and $P_2$ and $T_1$ and $T_2$ respectively. Assuming the volume V remains constant, it may be shown using equation (10) that the specific gas constant $R_s$ of the mixture in the chamber 162 may be estimated as $$R_s = \frac{V}{\Delta m}\left(\frac{P_1}{T_1} - \frac{P_2}{T_2}\right) \qquad (12)$$

In an alternative, derivative formulation, it may be shown using equation (10) that the specific gas constant $R_s$ of the mixture in the chamber 162 may be estimated as $$R_s = \frac{V\dot{P}(t)}{m(t)\dot{T}(t) + \dot{m}(t)T(t)} \qquad (13)$$

which may be approximated, assuming temperature remains roughly constant with time (i.e. its derivative is negligible), as:

$$R_s \approx \frac{V}{T}\frac{\dot{P}(t)}{\dot{m}(t)} \qquad (14)$$

The derivative formulation of Equation (14) may be more convenient than the integral formulation of Equation (12) if a "derivative pressure" sensor (providing a signal representative of the rate of change of pressure ($\dot{P}(t)$)) is used in place of the pressure sensor 166. Here, the equation, performed by the processor(s) 410, may use the known chamber volume V, measured temperature T, the measured mass flow rate $\dot{m}(t)$ and the measured rate of change of pressure $\dot{P}(t)$. The derivative formulation of Equation (14) returns an instantaneous value of the specific gas constant $R_s$ of the gas mixture and hence the oxygen concentration thereof, rather than a value based on measurements at two separate times.

Figure 7:
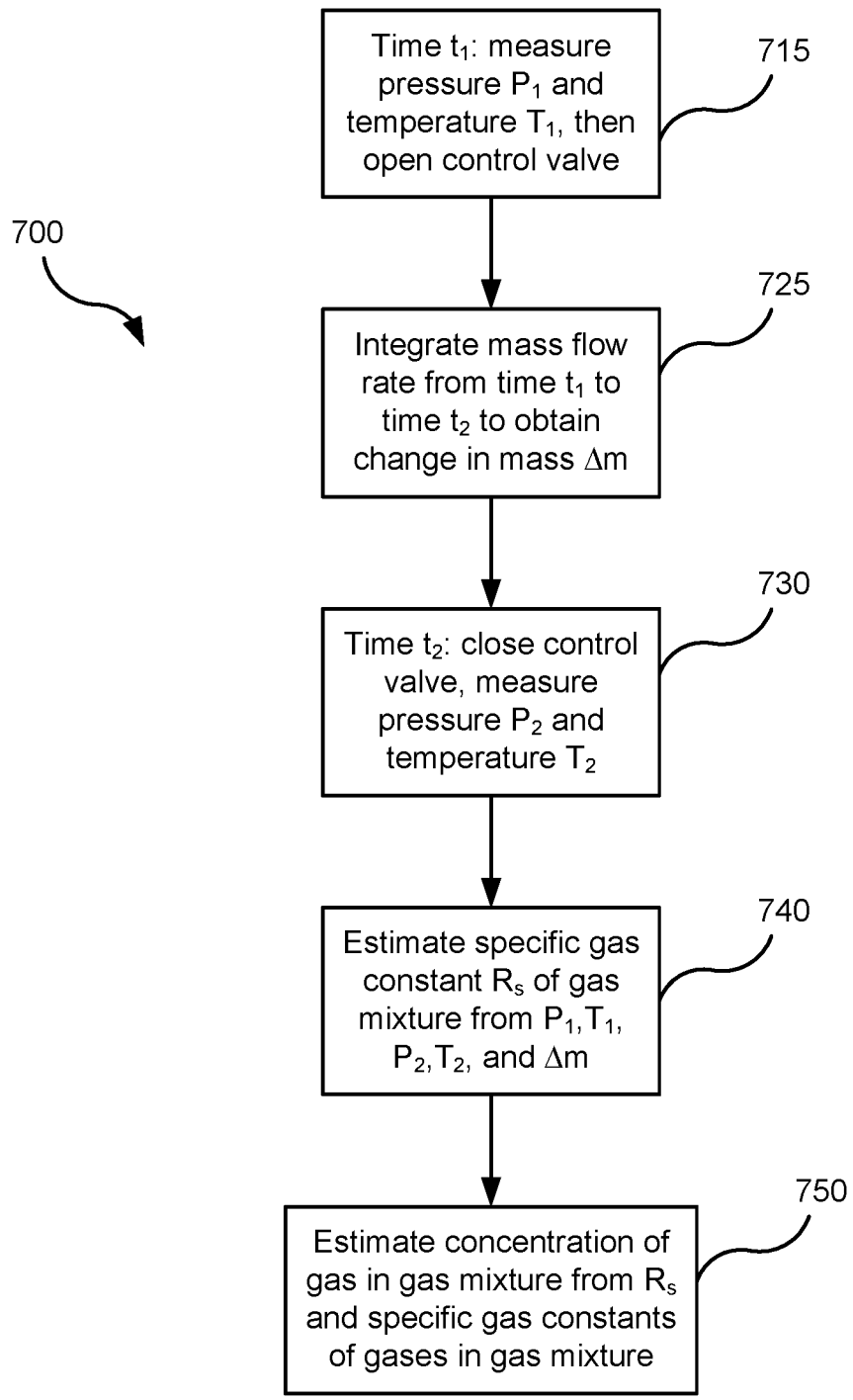
FIG. 7 is a flow chart illustrating a method that may be used to estimate the concentration of a gas in a gas mixture according to one form of the present technology.

FIG. 7 is a flow chart illustrating a method 700 that may be used to estimate the concentration of a gas in a gas mixture according to one form of the present technology. The method 700 may be implemented by program instructions stored in memory 420 or a carrier medium coupled to controller 400, and executed by one or more processors 410. While the method 700 will be described below in the context of the oxygen concentrator 100 generating oxygen enriched gas, it will be understood that neither the method 700 nor its associated oxygen sensor 165 is limited in application to oxygen concentrators, but may be applied to estimating concentrations of pure gases in other gas mixtures, such as two-gas mixtures or enriched mixtures of three or more gases.

In one implementation, the method 700 may be executed after the supply valve 160 is closed, so that no oxygen enriched gas is being delivered from the accumulator 106 to the chamber 162. The supply valve 160 may be re-opened after the end of the method 700 to allow oxygen enriched gas to build up once again in the expansion chamber 162.

The method 700 may start at a first time $t_1$, which, in the case of an oxygen concentrator, may coincide with the start of any delivery of a bolus of oxygen enriched gas to the user (e.g., detection of an onset of inhalation by evaluation of a signal (e.g., a drop in pressure) from a suitable sensor (e.g., pressure sensor 194)). At step 715, which takes place at time $t_1$, the pressure $P_1$ in the chamber 162 and the temperature $T_1$ in the chamber 162 are measured by the pressure sensor 166 and the temperature sensor 168 respectively. Step 715 then opens the control valve 175 to allow oxygen enriched gas to flow with respect to the chamber 162 (e.g., flow from the chamber 162 to the user). Step 725 integrates the mass flow rate signal $\dot{m}(t)$ provided by the mass flow sensor 185 over the time $t_1$ to a later time $t_2$ to give the change $\Delta m$ in mass of gas in the chamber 162 between $t_1$ and $t_2$. The later time $t_2$ may be chosen such that the interval between $t_1$ and $t_2$ is sufficient (e.g., large enough) that the difference in pressure between $P_1$ and $P_2$ is significantly above the noise floor of the pressure sensor 166.

Step 730 follows at the later time $t_2$, at which the pressure $P_2$ in the chamber 162 and the temperature $T_2$ in the chamber 162 are measured by the pressure sensor 166 and the temperature sensor 168 respectively. The timing of step 730 may generally coincide with closing of the control valve 175 such that it may be carried out when the control valve 175 has been closed, as illustrated in FIG. 7. In this implementation, the measurements of $P_2$ and $T_2$ may be made with some delay after $t_2$, though if there is an excessive delay in measuring the temperature $T_2$ the measurement may be inaccurate due to thermal conduction. Alternatively, step 730 may be carried out while the control valve 175 is still open. However, in this implementation the pressure $P_2$ in the chamber 162 and the temperature $T_2$ in the chamber 162 should be measured substantially simultaneously (i.e. with minimal delay) at the time $t_2$. This means there is less timing flexibility in this implementation.

The method may then include a determination or calculation of an estimate of gas concentration by applying one or more function(s) to any one, more or all of these measurements, such as to generate an indication of oxygen concentration as a processor and/or controller output. For example, at step 740 the measurements may be applied, such as using any form of the operations of equation (12) to estimate the specific gas constant $R_s$ of the oxygen enriched gas in the chamber 162 over the interval from $t_1$ to $t_2$. At step 750, any form of the operations of equation (7) may then be used to produce an estimate of the concentration $EC_i$ of oxygen in the oxygen enriched gas, having previously computed the constant K such as using any form of the operations of equation (8). If the gas mixture is a mixture of two gases, step 750 may use any form of the operations of equation (9) to estimate the concentration of a gas in the mixture.

If the "reciprocal" formulation of any form of the operations of equation (4) is used, step 750 may still use any form of the operations of equation (7) or (9) to estimate the concentration $EC_i$, except that the reciprocal $1/R_s$ and $1/R_{si}$ of each specific gas constant is substituted for each corresponding specific gas constant $R_s$ and $R_{si}$.

The pressure sensor 166, mass flow sensor 185, and the temperature sensor 168, in practice, may be imperfect, in the sense that their measured values are related to the true values by a linear relationship (i.e., the true quantity is equal to a sensor gain & times the measured quantity, where the sensor gain is unity for a perfect sensor). In addition, the true volume V of the chamber 162 may not be not known exactly, but may be a gain $\varepsilon_V$ times the measured value. Taking these gains into account, equation (12) may be rewritten as $$R_s = \frac{\varepsilon_V \varepsilon_P}{\varepsilon_m \varepsilon_T} \frac{V}{\Delta m} \left( \frac{P_1}{T_1} - \frac{P_2}{T_2} \right) \tag{15}$$

where V, $\Delta m$, P, and T represent measured quantities and $\varepsilon_V$, $\varepsilon_m$, $\varepsilon_P$, and $\varepsilon_T$ represent the respective gains for each quantity. The initial constant $$\frac{\varepsilon_V \varepsilon_P}{\varepsilon_m \varepsilon_T}$$

may be found by calibration, i.e. applying the method 700 to a gas, e.g. dry, fresh air, with a known specific gas constant $R_s$, and dividing the known specific gas constant $R_s$ by the specific gas constant estimated using any form of the operations of equation (12). The calibration could occur during manufacture and/or servicing. Calibration could also be performed by the oxygen concentrator, such as during system start up. For example, a process of the controller 400, including processor(s) 410, may be configured to control the valves of the system to ensure that chamber 162 contains a gas mixture with a known oxygen concentration e.g. 21% (atmospheric air).

The calibration constant $$\frac{\varepsilon_V \varepsilon_P}{\varepsilon_m \varepsilon_T}$$

may then be applied at step 740 using any form of the operations of equation (15) to give the true specific gas constant $R_s$ of the enriched mixture from the measured quantities.

The pressure sensor 166 may also have an offset $\varepsilon_{P0}$, which can be added to the measured value before scaling by the sensor gain $\varepsilon_P$ to obtain the true value of pressure. If the temperature difference between $T_1$ and $T_2$ is small, this offset $\varepsilon_{P0}$ will largely cancel out when the ratio difference $$\left(\frac{P_1}{T_1} - \frac{P_2}{T_2}\right)$$

is computed as part of step 740, and so does not need to be taken into account. However, if $T_1$ and $T_2$ differ significantly, the offset $\varepsilon_{P0}$ does need to be taken into account, via a modified version of equation (15):

$$R_s = \frac{\varepsilon_V \varepsilon_p}{\varepsilon_m \varepsilon_T} \frac{V}{\Delta m}\left(\frac{P_1}{T_1} - \frac{P_2}{T_2} + \varepsilon_{po}\left(\frac{1}{T_1} - \frac{1}{T_2}\right)\right) \quad (16)$$

The pressure sensor gain $\varepsilon_P$ and offset $\varepsilon_{P0}$ may be determined by making two pressure measurements at known temperatures on a known mass of gas of known specific gas constant $R_S$, and solving simultaneously for $\varepsilon_P$ and $\varepsilon_{P0}$ using two instances of equation (2). (The temperature sensor offset may be assumed to be negligible or can be zeroed prior to taking a temperature reading, since the temperature sensor offset is likely dominated by an Analogue to Digital Converter offset, which is easily zeroed.)

It is possible to zero the mass flow sensor 185 as part of step 715 before opening the control valve 175 (when the true mass flow rate is zero) to remove any offset from the mass flow sensor 185.

In an alternative form of the present technology, the mass flow sensor 185 may be positioned at the inlet to the chamber 162 rather than at the outlet as described above. The same method 700 may be used to estimate the concentration of a gas in the enriched gas, except that the supply valve 160 rather than the control valve 175 is opened at time $t_1$ and closed at time $t_2$, to allow oxygen enriched gas to flow into the chamber 162, while the control valve 175 is kept closed throughout this interval. The operations of the same equations as above may be used, except that $$\frac{P_1}{T_1} \text{ and } \frac{P_2}{T_2}$$

are interchanged in equation (12) (as $P_2$ will be greater than $P_1$). This form of the technology decouples the delivery of the bolus from the measurement of the oxygen concentration in the delivered gas but may still permit monitoring of oxygen concentration in the chamber 162 such as to provide an indication of in-chamber oxygen concentration and/or an indication of production oxygen concentration (e.g., a current production of the pressure swing adsorption process) rather than a delivery oxygen concentration indication as previously described in relation to the implementation of the mass flow sensor 185 being positioned downstream of the control valve 175 as illustrated in FIG. 4A.

In a further alternative form of the present technology, an inlet mass flow sensor (not shown) is positioned at the inlet to the chamber 162 in addition to the outlet mass flow sensor 185 at the outlet of the chamber 162. The same method 700 may be used to estimate the concentration of a gas in the enriched gas, except that the supply valve 160 may be open for some or all of the interval from the interval from $t_1$ to $t_2$. At step 725, the mass flow rate signal generated by the inlet mass flow sensor is integrated from $t_1$ to $t_2$ to give an inlet mass difference $\Delta m(in)$, which is subtracted from the outlet mass difference $\Delta m(out)$ obtained by integrating the mass flow rate signal generated by the outlet mass flow sensor 185 to give the net decrease in mass $\Delta m$. Alternatively, the difference between the mass flow rate signal generated by the outlet mass flow sensor 185 and the mass flow rate signal generated by the inlet mass flow sensor may be integrated from $t_1$ to $t_2$ to give the net decrease in mass $\Delta m$.

In an alternative implementation of the oxygen sensor 165, a flow rate sensor may be used in place of any of the mass flow sensor(s) 185 in any of the positions previously described, and the flow rate measurement generated by the flow rate sensor(s) may be converted to a mass flow rate by multiplying by the density of the enriched mixture.

Oxygen Sensor Based on Thermal Properties

If a special-purpose sensor adapted to measuring the concentration $EC_i$ of one specific non-removed gas in the enriched mixture is employed, the concentration $EC_j$ of any other non-removed gas in the enriched mixture may be estimated as $$EC_j = \frac{C_j}{C_i} EC_i \quad (17)$$

In the example of oxygen enrichment of dry, fresh air where $C_2=0.21$ (oxygen) and $C_3=0.01$ (argon), an argon concentration sensor may be used to measure the concentration $EC_3$ of argon in the oxygen enriched gas, the concentration $EC_2$ of oxygen may be estimated as $21*EC_3$.

Thermal properties are particularly suitable for sensing argon concentration in a mixture of nitrogen, oxygen, and argon (such as oxygen enriched gas) because argon's thermal properties are significantly different from those of oxygen and nitrogen. In fact, the thermal conductivity of oxygen is so similar to that of nitrogen (both being around 0.026 watts per metre kelvin at room temperature and pressure (RTP)) that dry air (or oxygen enriched gas) may be treated for thermal purposes as being a binary mixture of argon (whose thermal conductivity is about 0.018 watts per metre kelvin at RTP) and oxygen/nitrogen.

According to one model [1], the thermal conductivity $k_{12}$ of a binary gas mixture of fractional concentrations $c_1$ and $c_2$ may be estimated as:

$$k_{12} = \frac{k_1 k_2}{2(c_1 k_2 + c_2 k_1)} + \frac{c_1 k_1 + c_2 k_2}{2} \quad (18)$$

where $k_1$ is the thermal conductivity of the first gas in the mixture, and $k_2$ is the thermal conductivity of the second gas in the mixture. If the thermal conductivity $k_{12}$ of a binary gas mixture can be estimated, it may be shown using equation (18) and the relation $c_1=1-c_2$ that the fractional concentration $c_2$ of the second gas in the mixture may be obtained by solving a quadratic equation in $c_2$:

$$\alpha c_2^2 + \beta c_2 + \gamma = 0 \quad (19)$$

with coefficients given by:

$$\alpha = (k_1 - k_2)^2$$

$$\beta = 2k_{12}(k_1 - k_2) - (k_1 - k_2)^2 \quad (20)$$

$$\gamma = 2k_2(k_{12} - k_1)$$

Applying this approach to estimating the concentration of oxygen in oxygen enriched gas, $k_1$ is the thermal conductivity of oxygen/nitrogen (0.026), $k_2$ is the thermal conductivity of argon (0.018), $k_{12}$ is the estimated thermal conductivity of the oxygen enriched gas, and $c_2$ is the concentration (equal to $EC_3$) of argon in the oxygen enriched gas. Solving the quadratic in equation (19) for $c_2$ gives the concentration $EC_3$ of argon in the oxygen enriched gas. The concentration $EC_2$ of oxygen in the oxygen enriched gas may then be estimated as $21*EC_3$.

In an alternative implementation, a calibration phase may be undertaken in which plural oxygen enriched gases with various, known concentrations of oxygen and argon spanning the expected range (21% to 99% oxygen) have their respective thermal conductivities measured, and a lookup table created tabulating the concentration of argon against the thermal conductivity of each oxygen enriched gas. Then during measurement, a value of argon concentration may be interpolated from the values in the lookup table, such as in a carrier medium, data storage medium or other memory accessible to the controller/processor of the oxygen concentrator, corresponding to the nearest values of thermal conductivity to the estimated thermal conductivity of the oxygen enriched gas.

As described above, the concentration $EC_2$ of oxygen in the oxygen enriched gas may then be computed as 21 times the concentration $EC_3$ of argon in the oxygen enriched gas.

Figure 8:
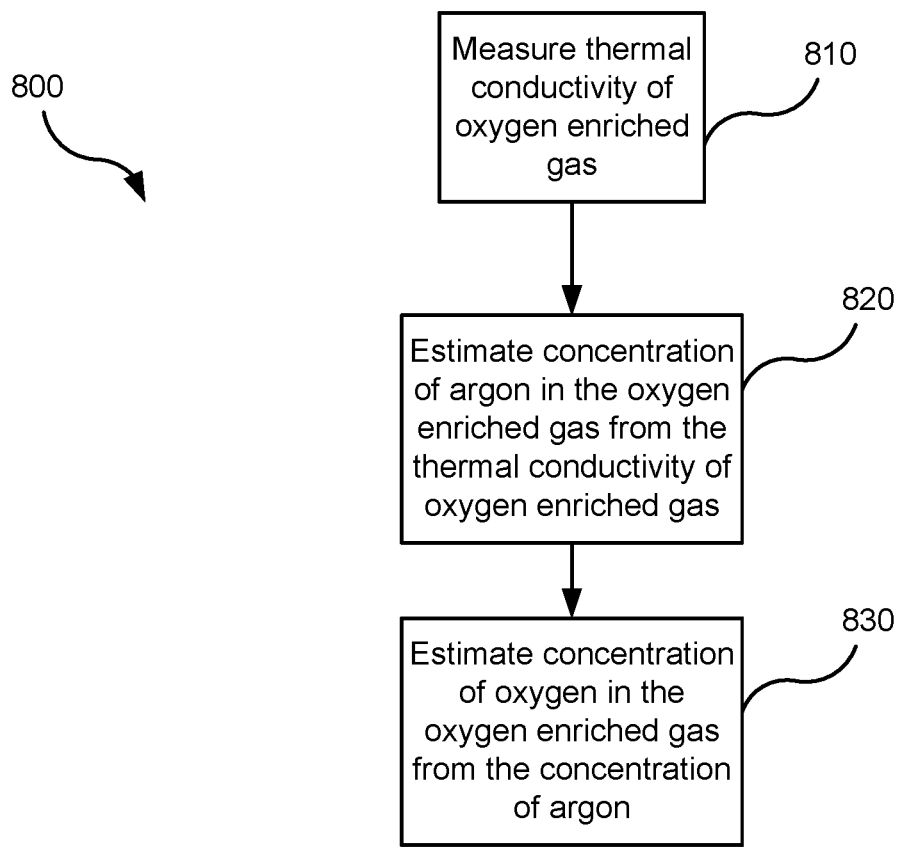
FIG. 8 is a flow chart illustrating a method of estimating the concentration of oxygen in oxygen enriched gas.

FIG. 8 is a flow chart illustrating a method 800 of estimating the concentration of oxygen in oxygen enriched gas generated by an oxygen concentrator 100. The method 800 may be implemented by program instructions stored in memory 420 or a carrier medium coupled to controller 400, and executed by one or more processors 410. The method 800 starts at step 810, which measures the thermal conductivity $k_{12}$ of the oxygen enriched gas. Example implementations of step 810 are described below. Step 820 follows, which estimates the concentration $EC_3$ of argon in the oxygen enriched gas from the measured thermal conductivity $k_{12}$ of the oxygen enriched gas by solving the quadratic equation (19) for $c_2$, or interpolating and/or accessing values from a calibration lookup table as described above. Finally step 830 estimates the concentration $EC_2$ of oxygen in the oxygen enriched gas by multiplying the concentration $EC_3$ of argon by 21.

Any of the estimates of gas concentration (e.g., oxygen concentration) may then be output by the one or more processors 410 such as to provide an indication of oxygen concentration as previously described. The indication may be stored over time of use of the oxygen concentrator such as to provide a log and/or display of produced, contained and/or delivered oxygen concentration. In some versions, the estimate may serve as a basis for a control operation of the oxygen concentrator, such as by evaluation of the estimate with one or more thresholds. For example, it may serve as a control parameter to operate the controller such as to stop, begin, continue, or adjust parameters of the pressure adsorption process previously described (e.g., controlling the compression system and/or valves 122, 132, 124, 134, 152, 154, 160, etc.) based on a comparison between the estimate and one or more thresholds. For example, if such an estimate falls below a threshold or rises above a threshold, a control signal may be generated in response to the threshold-related comparison. Optionally, it may serve as a control parameter for activation of an alarm such as to evaluate the production, containment and/or delivery of oxygen concentration. For example, if such an estimate falls below a threshold, an alarm (e.g., light and/or sound) may be triggered by a signal generated in response to the threshold-related comparison.

Figure 9:
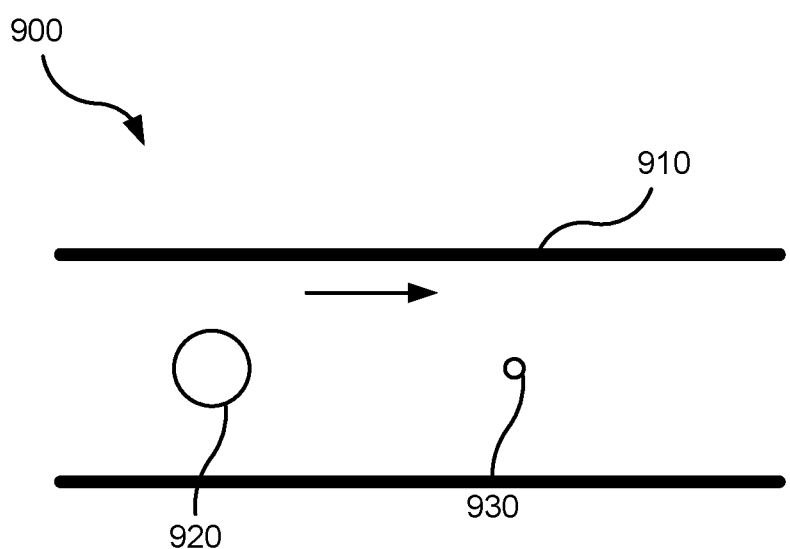
FIG. 9 is a schematic of a device for measuring thermal conductivity of a flow of gas.

FIG. 9 is a schematic illustration of a device 900 for measuring the thermal conductivity of a flow of gas through a pipe 910 (e.g., a conduit or gas flow path of the oxygen concentrator) in the direction indicated by the arrow, in one implementation of step 810. The element 920 is a reference temperature sensor that measures the temperature of the gas. The reference sensor of element 920 may have a large enough thermal mass not to be affected by the cooling effect of the gas flow or changes in the thermal conductivity of the gas. For example, the reference sensor of element 920 may be an encapsulated silicon bandgap-based temperature sensor.

The element 930, shown downstream of the reference sensor of element 920, is also a temperature sensor, with much smaller thermal mass than the reference sensor of element 920. For example, the sensor of element 930 may be an NTC thermistor that is self-heated by power (e.g., continuous power) being delivered to it. The temperature returned by the sensor of element 930 is a function of the actual temperature of the gas, the cooling effect of the gas flow past the sensor of element 930 (a function of the flow rate), and the thermal conductivity of the gas (which for a gas mixture is a function of the concentrations of the gases in the mixture, as described above). It follows that the difference $\Delta T$ between the temperature measured by the sensor of element 930 and the temperature measured by the reference sensor 920 is dependent on the flow rate and thermal conductivity of the gas. If the flow rate is measured by a separate flow rate sensor (not shown) in the pipe 910, the thermal conductivity of the gas may be inferred from the temperature difference $\Delta T$ and the measured flow rate.

The element 930 may alternatively be placed upstream of the reference sensor of element 920, or level with it but transversely separated across the gas flow (e.g., perpendicular to flow direction), so that airflow over the element 930 is not disrupted by the larger reference sensor of element 920.

Additionally, or alternatively, it may be possible to determine the thermal conductivity of the gas by other means when the flow rate in the pipe 910 is zero. For example, when a control valve controlling the flow of gas through the pipe 910 is turned off, the flow rate may be assumed to be zero. The thermal conductivity of the gas may be inferred from the temperature difference $\Delta T$ when the flow rate is zero. Thus, in such a case, the separate flow rate sensor (not shown) is not needed such as when the determinations (e.g., the measurements of the temperatures for difference $\Delta T$) remain timed with the closed operations of the valve controlling the flow of gas through the pipe 910.

The sensor of element 930 preferably has a low enough thermal mass to respond fast enough to changes in the concentrations and the flow rate. For a POC application, the flow rate and concentration changes are slow, hence the response time does not need to be very fast. For example, a response time in the order of 1 to 10 seconds may be fast enough.

To implement step 810 in the oxygen concentrator 100, the device 900 may be inline with the flow of oxygen enriched gas from the accumulator 106. For example, the oxygen sensor 165 may take the form of the device 900, in which case the temperature sensor 168 is the reference sensor 920 and the pressure sensor 166 may be omitted. Alternatively, the device 900 may be located in the conduit 192 of the oxygen concentrator 100.

In an alternative implementation of step 810, a mass flow sensor with a thermal conductivity measurement capability may be used to implement the mass flow sensor 185 in the oxygen concentrator 100. Such a "thermal mass flow sensor" is disclosed in US Patent Publication no. US2018/0143051, to Honeywell International Inc, the entire content of which is herein incorporated by reference. In such an implementation, the thermal conductivity measurement capability is employed to provide the thermal conductivity measurement, while the mass flow rate sensing capability would be used to provide the mass flow rate measurements utilized by the controller 400 as described above.

Figure 10A:
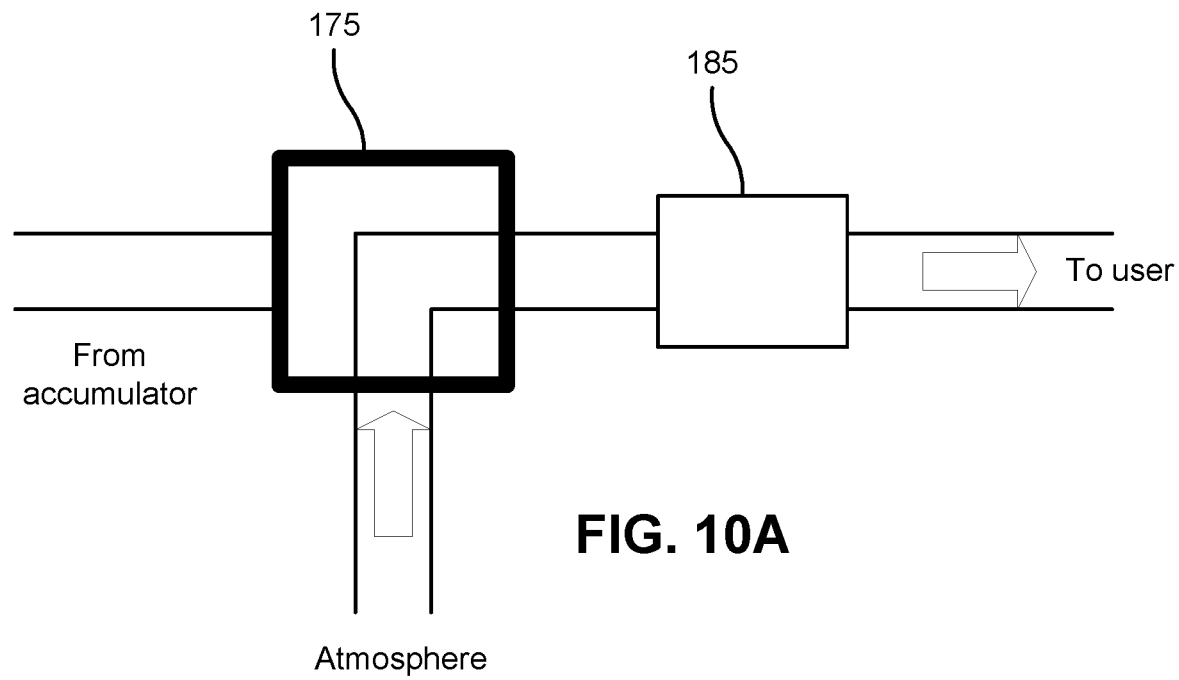
FIGS. 10A and 10B show a schematic illustrating operation of a control valve in an implementation of step 810 of the method of FIG. 8.
Figure 10B:
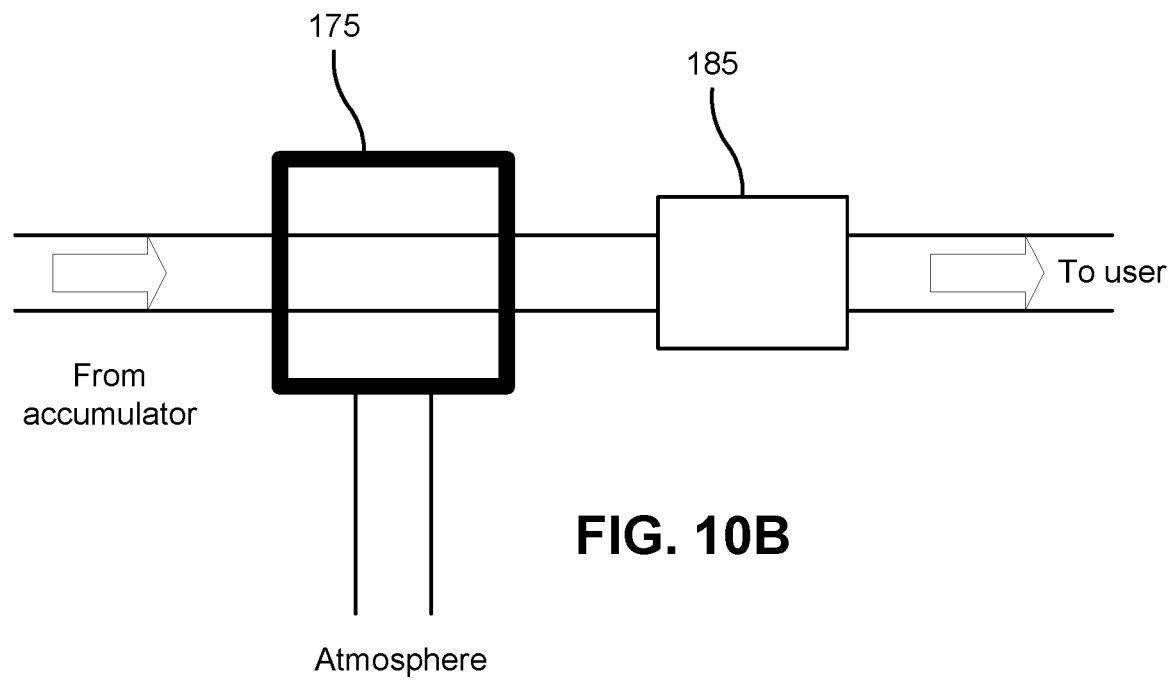

FIGS. 10A and 10B illustrate an optional variant of this alternative implementation. In the example, the control valve 175 may be a three-way valve with common output to the thermal mass flow sensor 185, and the third output to atmosphere. In between boluses, the operation of the control valve 175 may be set by the controller to be configured as shown in FIG. 10A, connecting the atmosphere to the thermal mass flow sensor 185. The thermal mass flow sensor 185 may then serve as an inhalation sensor to detect the onset of inhalation. Thus, pressure sensor 194 may optionally be omitted as the thermal mass flow sensor 185 may be a suitable alternate sensor. Thus, a drop in pressure in the output conduit 192 caused by the onset of inhalation will cause the thermal mass flow sensor 185 to register an increase in flow rate, and thereby generate a signal which may be evaluated by the controller to generate a bolus control signal for triggering bolus delivery. Flow rate sensors such as the thermal mass flow sensor 185 have generally superior offset stability to pressure sensors and this variant may therefore give a more accurate indication of the onset of inhalation than if the pressure sensor 194 were used. Note however that without a connection to atmosphere, an inline flow rate sensor 185 cannot be used to detect the onset of inhalation because insufficient flow is generated by the pressure drop as long as control valve 175 is closed.

During bolus delivery, control valve 175 may be set by the controller to be configured as shown in FIG. 10B, connecting the accumulator 106 to the user via thermal mass flow sensor 185. The thermal mass flow sensor 185 may monitor the amplitude profile of the delivered bolus as well as its oxygen concentration. This variant alternative implementation can provide a single sensor solution yielding both oxygen concentration measurement and bolus triggering control, and may further provide the option of bolus profile control (e.g., by the controller setting the bolus profile as measured by the thermal mass flow sensor 185 and controlled by the operation of a delivery valve (e.g., control valve 175)).

Figure 11A:
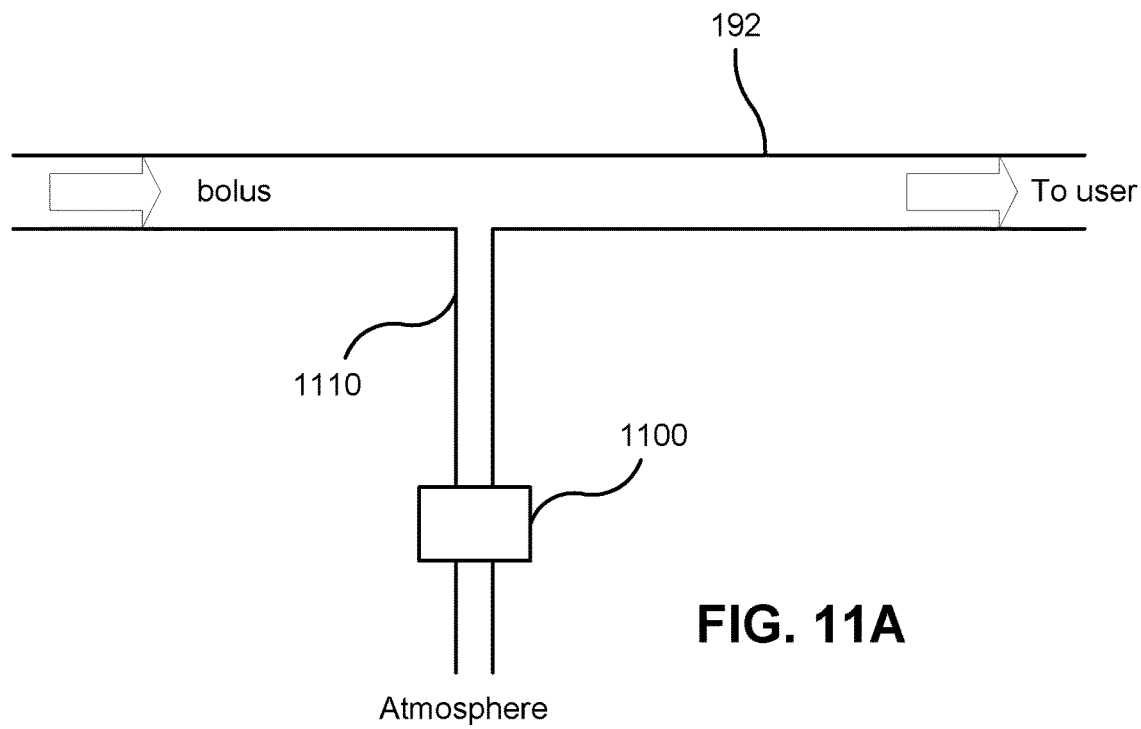
FIG. 11A is a schematic of an alternative implementation of step 810 of the method of FIG. 8.

A further alternative implementation of step 810 is illustrated in FIG. 11A. A thermal mass flow sensor 1100 is positioned on a tap 1110 to atmosphere in the conduit 192, rather than inline with the main flow of oxygen enriched gas, as the mass flow sensor 185 is shown positioned in FIG. 4A. In one such implementation, the tap 1110 to atmosphere may be a section of high impedance tubing (e.g., 0.1 mm internal diameter). A thermal mass flow sensor 1100 positioned in this manner may also serve as an alternative to the pressure sensor 194 for control of triggering bolus delivery. In this regard, a drop in pressure in the output conduit 192 caused by the onset of inhalation will cause the thermal mass flow sensor 1100 to register an increase in flow rate (i.e., air drawn into the tap 1110 from atmosphere), which can then serve as a control indication as previously discussed for triggering bolus delivery. Although the tap 1110 in FIG. 11A is to atmosphere, the tap 1110, via thermal mass flow sensor 1100, may be to the internal space (internal atmosphere) of the oxygen concentrator 100. Nevertheless, a tap to external atmosphere is preferable since the concentrator interior can be at a pressure that is somewhat elevated relative to external atmosphere (i.e., the environment about the housing of the oxygen concentrator).

In some versions, during bolus delivery, the thermal mass flow sensor 1100 may monitor the amplitude profile of the delivered bolus by diverting a small portion of the output flow of oxygen enriched gas. This small portion of the bolus is sensed by the mass flow sensor 1100 as it passes through the sensor and out the tap 1110 to atmosphere. Thus, the bolus profile may be controlled by estimating the delivered bolus amplitude profile from the measured diverted portion of the bolus at the mass flow sensor 1100 and adjusting operation of a delivery valve, e.g. the control valve 175. The high impedance tubing of the tap 1110 may be configured to limit the amount of oxygen enriched gas diverted from the user so that the diverted amount is some amount above the noise floor of the thermal mass flow sensor. Thus, the impedance of the tap 1110 restricts flow through the tap to favor delivery of the oxygen enriched gas to the user from the accumulator to the outlet 174 of the oxygen concentrator. The thermal mass flow sensor 1100 then can also monitor the argon concentration and hence oxygen concentration of the bolus via thermal conductivity as described above. Thus, this further alternative implementation also provides a single sensor solution that may permit both oxygen concentration measurement, and triggering control, and optionally bolus profile control, and may not need a multi-port control valve (e.g., three or more ports) such as in the version of FIGS. 10A and 10B.

Figure 11B:
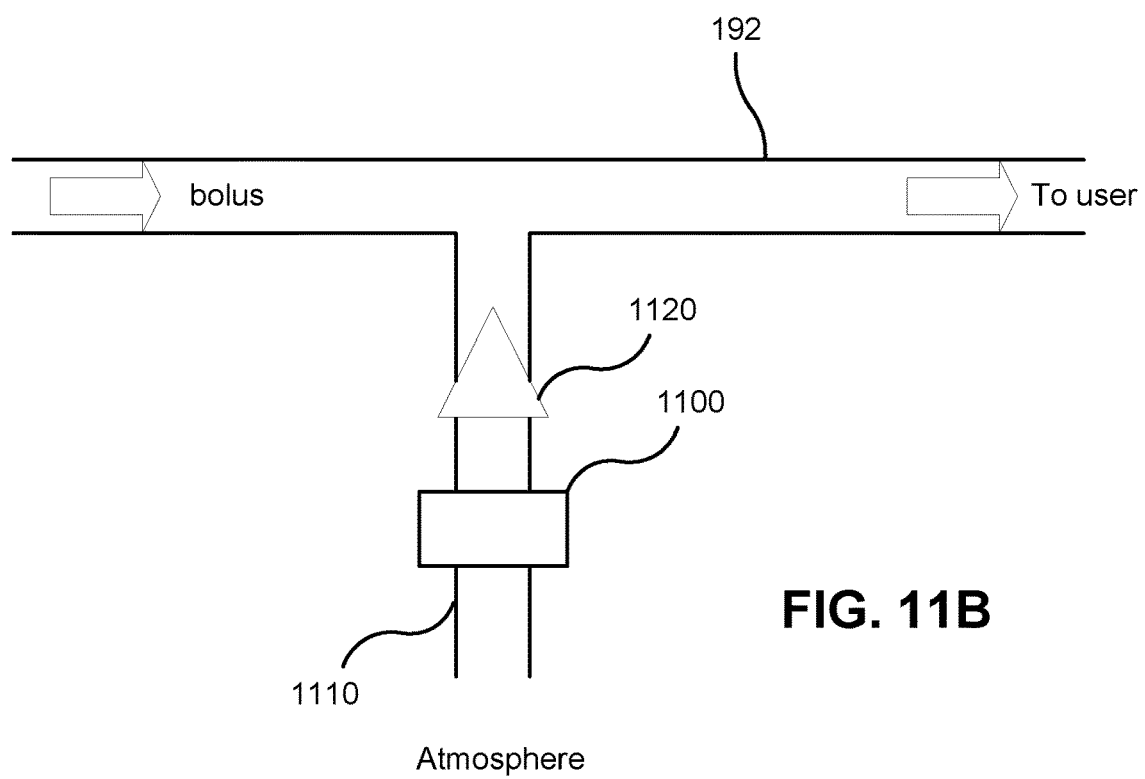
FIG. 11B is a schematic of a further alternative implementation of step 810 of the method of FIG. 8.

In a variant of this further alternative implementation illustrated in FIG. 11B, a passive valve 1120, such as a flap valve, may be positioned in the tap 1110 with the thermal mass flow sensor 1100. The passive valve 1120 is oriented to more readily allow flow in the direction from atmosphere through the tap 1110 and the thermal mass flow sensor 1100 to the user at the onset of inhalation, while impeding (less readily allowing) flow in the opposite direction through the tap 1110 to atmosphere during bolus delivery. Such a passive valve permits different flow rates through the passive valve depending on the direction of flow, while permitting flow in both directions through the valve. This variant also gives a single sensor solution providing both oxygen concentration measurement, and triggering control, while allowing lower impedance tubing to be used for the tap 1110 than the implementation of FIG. 11A, which can increase the sensitivity of the flow rate measurement to detect the onset of inhalation, and/or prevent a significant diversion of the delivered bolus of oxygen enriched gas to atmosphere via the thermal mass flow sensor 1110. This variant therefore cannot monitor the flow rate of the bolus, but does permit sufficient flow during bolus delivery to allow the oxygen concentration of the bolus to be measured.

At the onset of inhalation, the pressure in the conduit 192 may still be slightly positive with respect to atmosphere. The passive valve 1220 may therefore be configured with a small dead band at low positive pressures to allow a small but detectable back flow through the mass flow sensor 1100 to atmosphere to trigger bolus delivery, while still impeding flow at the large positive pressures during bolus delivery.

In a hybrid implementation, the passive valve 1120 and the high impedance tubing may both be present in parallel with one another and in series with the thermal mass flow sensor 1100. The passive valve 1120 would allow flow in the direction from atmosphere to the user at the onset of inhalation to trigger bolus delivery as in FIG. 11B, while the high impedance tubing diverts a small portion of the bolus of oxygen enriched gas during bolus delivery. This small portion of the bolus may be sensed by the mass flow sensor 1100 as it passes out to atmosphere to monitor oxygen concentration and bolus profile. Thus, this hybrid implementation also provides a single sensor solution that may permit both oxygen concentration measurement, and triggering control, and optionally bolus profile control.

General Remarks

In the present disclosure, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the technology may be apparent to those skilled in the art in view of this description. Accordingly, this description is to be construed as illustrative only and is for the purpose of teaching those skilled in the art the general manner of carrying out the technology. It is to be understood that the forms of the technology shown and described herein are to be taken as embodiments. Elements and materials may be substituted for those illustrated and described herein, parts and processes may be reversed, and certain features of the technology may be utilized independently, all as would be apparent to one skilled in the art after having the benefit of this description of the technology. Changes may be made in the elements described herein without departing from the spirit and scope of the technology as described in the following claims.

Label List

| | |
|---|---|
| oxygen concentrator | 100 |
| inlets | 101 |
| accumulator | 106 |
| compression system inlets | 107 |
| muffler | 108 |
| inlet valve | 122 |
| inlet valve | 124 |
| outlet | 130 |
| outlet valve | 132 |
| muffler | 133 |
| outlet valve | 134 |
| check valves | 142 |
| check valves | 144 |
| flow restrictors | 151 |
| valve | 152 |
| flow restrictors | 153 |
| valves | 154 |
| flow restrictor | 155 |
| valves | 160 |
| chamber | 162 |
| oxygen sensor | 165 |
| pressure sensor | 166 |
| temperature sensor | 168 |
| outer housing | 170 |
| fan | 172 |
| outlet | 173 |
| outlet port | 174 |
| control valve | 175 |
| power supply | 180 |
| mass flow sensor | 185 |
| filter | 187 |
| connector | 190 |
| outlet conduit | 192 |

-continued

| | |
|---|---|
| pressure sensor | 194 |
| compression system | 200 |
| compressor | 210 |
| compressor outlet | 212 |
| motor | 220 |
| external armature | 230 |
| air transfer device | 240 |
| compressor outlet conduit | 250 |
| compression system | 300 |
| canister | 302 |
| canisters | 304 |
| base | 315 |
| outlet | 325 |
| gases | 327 |
| controller | 400 |
| Processor(s) | 410 |
| internal memory | 420 |
| control panel | 600 |
| input port | 605 |
| power button | 610 |
| button | 620 |
| button | 622 |
| button | 624 |
| button | 626 |
| button | 630 |
| button | 635 |
| altitude button | 640 |
| battery check button | 650 |
| LED | 655 |
| method | 700 |
| airway delivery device | 710 |
| mouthpiece | 720 |
| step | 715 |
| step | 725 |
| step | 730 |
| step | 740 |
| step | 750 |
| method | 800 |
| step | 810 |
| step | 820 |
| step | 830 |
| device | 900 |
| pipe | 910 |
| element | 920 |
| element | 930 |
| thermal mass flow sensor | 1100 |
| tap | 1110 |
| passive valve | 1120 |

REFERENCES

1. *Thermal conductivity of binary mixtures of gases*, E. S. Udoetok. *Frontiers in Heat and Mass Transfer*, Vol. 4, 023008 (2013).

What is claimed is:

1. An oxygen concentrator apparatus comprising:
an outlet, the outlet suitable for pneumatic coupling with a delivery device, the delivery device for delivering, in use, oxygen enriched gas to a user;
at least two canisters including gas separation adsorbent, the gas separation adsorbent configured for gas separation of at least some nitrogen from air in the at least two canisters to produce the oxygen enriched gas;
a compression system comprising a compressor coupled to at least one of the canisters to compress air during operation to promote the gas separation;
an accumulator coupled to one or more of the canisters, to accumulate the oxygen enriched gas produced in one or more of the canisters during use, the accumulator pneumatically coupled to the outlet;
a tap to atmosphere in a pneumatic path between the outlet and the accumulator, a flow rate sensor pneumatically coupled to the accumulator and the outlet, the flow rate sensor configured to generate at least a flow rate signal; and a controller, including one or more processors, and a set of valves coupled to the controller, the controller configured to control operation of the set of valves to (a) produce the oxygen enriched gas into the accumulator and (b) release the produced oxygen enriched gas from the accumulator in at least one bolus, the controller further configured to:

receive the flow rate signal from the flow rate sensor;
evaluate the flow rate signal to detect an onset of inhalation by the user when in use;
control a delivery valve of the set of valves to release, to the outlet, the at least one bolus based on the detected onset from the evaluation of the flow rate signal from the flow rate sensor; and
monitor the flow rate signal during release of the at least one bolus.

2. The oxygen concentrator apparatus of claim 1 wherein the flow rate sensor is a thermal mass flow sensor, and the controller is further configured to:

receive a thermal conductivity signal from the thermal mass flow sensor; and
estimate concentration of oxygen of the oxygen enriched gas based on the received thermal conductivity signal from the thermal mass flow sensor.

3. The oxygen concentrator apparatus of claim 2 wherein the controller is further configured to:

evaluate the estimated concentration of oxygen; and
generate an alarm signal based on the evaluation of the estimated concentration of oxygen.

4. The oxygen concentrator apparatus of claim 1 wherein the controller is further configured to control the delivery valve to adjust an amplitude profile of the at least one bolus based on the monitored flow rate signal from the flow rate sensor.

5. The oxygen concentrator apparatus of claim 1 wherein the delivery valve comprises a multi-port valve including a first port pneumatically coupled to the tap, a second port pneumatically coupled to the outlet, and a third port pneumatically coupled to the accumulator.

6. The oxygen concentrator apparatus of claim 5 wherein, to sense the onset of inhalation, the controller is further configured to set the delivery valve to pneumatically couple (1) the first port to the tap with (2) the second port to the outlet.

7. The oxygen concentrator apparatus of claim 5 wherein, to release the at least one bolus, the controller is further configured to set the delivery valve to pneumatically couple (1) the second port to the outlet with (2) the third port to the accumulator.

8. The oxygen concentrator apparatus of claim 1, wherein the flow rate sensor is positioned proximate to the tap to measure flow rate through the tap from atmosphere to the pneumatic path.

9. The oxygen concentrator apparatus of claim 8 wherein the tap comprises a high impedance tubing configured to limit amount of flow through the tap during bolus release.

10. The oxygen concentrator apparatus of claim 8 further comprising a passive valve in parallel with the tap to atmosphere, wherein the passive valve is configured to permit different flow rates through the passive valve depending on direction of flow through the passive valve.

11. A method of a controller of an oxygen concentrator apparatus, the method comprising:

receiving a flow rate signal in the controller, the flow rate signal generated with a flow rate sensor that is pneumatically coupled to (1) an accumulator for oxygen enriched gas produced by the oxygen concentrator apparatus, and (2) an outlet for the oxygen enriched gas; and
evaluating, in the controller, the flow rate signal to detect an onset of inhalation by a user of the oxygen concentrator apparatus;
controlling, by the controller, a delivery valve to release, to the outlet, at least one bolus of oxygen enriched gas based on the detected onset from the evaluation of the flow rate signal from the flow rate sensor; and
monitoring, in the controller, the flow rate signal during release of the at least one bolus.

12. The method of claim 11 wherein the flow rate sensor is a thermal mass flow sensor, the method further comprising:

receiving, in the controller, a thermal conductivity signal from the thermal mass flow sensor; and
estimating in the controller, concentration of oxygen of the oxygen enriched gas based on the received thermal conductivity signal from the thermal mass flow sensor.

13. The method of claim 12 further comprising:

evaluating, in the controller, the estimated concentration of oxygen; and
generating, with the controller, an alarm signal based on the evaluation of the estimated concentration of oxygen.

14. The method of claim 11 further comprising controlling, with the controller, the delivery valve to adjust an amplitude profile of the at least one bolus based on the monitored flow rate signal from the flow rate sensor.

15. The method of claim 11 wherein the delivery valve comprises a multi-port valve including a first port pneumatically coupled to a tap, a second port pneumatically coupled to the outlet, and a third port pneumatically coupled to the accumulator.

16. The method of claim 15 wherein, to sense the onset of inhalation, the controller controls setting of the delivery valve to pneumatically couple (1) the first port to the tap with (2) the second port to the outlet.

17. The method of claim 15 wherein, to release the at least one bolus, the controller controls setting of the delivery valve to pneumatically couple (1) the second port to the outlet with (2) the third port to the accumulator.

18. The method of claim 11 wherein the flow rate sensor is positioned proximate to a tap to measure flow rate through the tap from atmosphere to a pneumatic path, wherein the tap is pneumatically coupled to atmosphere and the pneumatic path is between the outlet and the accumulator.

19. The method of claim 18 wherein the tap comprises a high impedance tubing configured to limit amount of flow through the tap during bolus release.

20. The method of claim 18 wherein a passive valve is in parallel with the tap to atmosphere, wherein the passive valve is configured to permit different flow rates through the passive valve depending on direction of flow through the passive valve.

* * * * *